(12) United States Patent
Shanley

(10) Patent No.: US 7,179,289 B2
(45) Date of Patent: *Feb. 20, 2007

(54) EXPANDABLE MEDICAL DEVICE FOR DELIVERY OF BENEFICIAL AGENT

(75) Inventor: John F. Shanley, Redwood City, CA (US)

(73) Assignee: Conor Medsystems, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/862,963

(22) Filed: Jun. 7, 2004

(65) Prior Publication Data

US 2004/0225350 A1 Nov. 11, 2004

Related U.S. Application Data

(63) Continuation-in-part of application No. 10/456,292, filed on Jun. 5, 2003, which is a continuation of application No. 09/688,092, filed on Oct. 16, 2000, now abandoned, which is a continuation-in-part of application No. 09/183,555, filed on Oct. 29, 1998, now Pat. No. 6,241,762.

(60) Provisional application No. 60/079,881, filed on Mar. 30, 1998.

(51) Int. Cl.
*A61F 2/06* (2006.01)

(52) U.S. Cl. ............... 623/1.42; 623/1.15; 623/1.16

(58) Field of Classification Search ............... 623/1.15, 623/1.16, 1.17, 1.34, 1.39, 1.42, 1.43, 1.46; 606/194

See application file for complete search history.

(56) References Cited

U.S. PATENT DOCUMENTS

| 4,889,119 A | 12/1989 | Jamiolkowski et al. |
|---|---|---|
| 4,916,193 A | 4/1990 | Tang et al. |
| 5,085,629 A | 2/1992 | Goldberg et al. |
| 5,139,480 A | 8/1992 | Hickle et al. |
| 5,160,341 A | 11/1992 | Brenneman et al. |
| 5,419,760 A | 5/1995 | Narciso |
| 5,441,515 A | 8/1995 | Khosravi et al. |
| 5,443,458 A | 8/1995 | Eury |

(Continued)

FOREIGN PATENT DOCUMENTS

DE 20200220 3/2002

(Continued)

OTHER PUBLICATIONS

Jennifer L. West, "Drug Delivery—Pulsed Polymers". Nature Materials, vol. 2, Nov. 2003, pp. 709-710.

(Continued)

*Primary Examiner*—David H. Willse
*Assistant Examiner*—Javier G. Blanco
(74) *Attorney, Agent, or Firm*—Cindy A. Lynch

(57) ABSTRACT

An expandable medical device has a plurality of elongated struts, the plurality of elongated struts being joined together to form a substantially cylindrical device. The device is expandable from a cylinder having a first diameter to a cylinder having a second diameter, and the plurality of struts each having a strut width in a circumferential direction. At least one of the struts includes at least one opening extending at least partially through a thickness of the strut. A beneficial agent can be loaded into the opening within the strut. The expandable medical device may further include a plurality of ductile hinges formed between the elongated struts, the ductile hinges allowing the cylindrical device to be expanded or compressed from the first diameter to the second diameter by deformation of the ductile hinges.

34 Claims, 9 Drawing Sheets

U.S. PATENT DOCUMENTS

| | | |
|---|---|---|
| 5,464,450 A | 11/1995 | Buscemi et al. |
| 5,500,013 A | 3/1996 | Buscemi et al. |
| 5,609,629 A | 3/1997 | Fearnot et al. |
| 5,670,161 A | 9/1997 | Healy et al. |
| 5,769,883 A | 6/1998 | Buscemi et al. |
| 5,797,898 A | 8/1998 | Santini et al. |
| 5,824,049 A | 10/1998 | Ragheb et al. |
| 5,873,904 A | 2/1999 | Ragheb et al. |
| 5,972,027 A | 10/1999 | Johnson |
| 5,992,769 A | 11/1999 | Wise |
| 6,071,305 A | 6/2000 | Brown et al. |
| 6,096,070 A | 8/2000 | Ragheb et al. |
| 6,123,861 A | 9/2000 | Santini et al. |
| 6,156,062 A | 12/2000 | McGuinness |
| 6,203,569 B1 * | 3/2001 | Wijay ................ 623/1.15 |
| 6,206,915 B1 | 3/2001 | Fagan et al. |
| 6,241,762 B1 | 6/2001 | Shanley |
| 6,254,632 B1 | 7/2001 | Wu et al. |
| 6,273,908 B1 | 8/2001 | Ndondo-Lay |
| 6,273,913 B1 | 8/2001 | Wright et al. |
| 6,287,332 B1 | 9/2001 | Bolz et al. |
| 6,290,673 B1 | 9/2001 | Shanley |
| 6,293,967 B1 | 9/2001 | Shanley |
| 6,299,604 B1 | 10/2001 | Ragheb et al. |
| 6,331,189 B1 | 12/2001 | Wolinsky et al. |
| 6,334,871 B1 | 1/2002 | Dor et al. |
| 6,338,739 B1 | 1/2002 | Datta et al. |
| 6,368,346 B1 | 4/2002 | Jadhav |
| 6,379,381 B1 | 4/2002 | Hossainy et al. |
| 6,387,124 B1 | 5/2002 | Buscemi et al. |
| 6,423,092 B2 | 7/2002 | Datta et al. |
| 6,491,666 B1 | 12/2002 | Santini et al. |
| 6,506,437 B1 | 1/2003 | Harish et al. |
| 6,537,256 B2 | 3/2003 | Santini et al. |
| 6,551,838 B2 | 4/2003 | Santini et al. |
| 6,558,733 B1 | 5/2003 | Hossainy |
| 6,562,065 B1 | 5/2003 | Shanley |
| 6,565,602 B2 | 5/2003 | Rolando et al. |
| 6,585,764 B2 | 7/2003 | Wright et al. |
| 6,605,110 B2 * | 8/2003 | Harrison ................ 623/1.15 |
| 6,635,082 B1 | 10/2003 | Hossainy et al. |
| 6,656,162 B2 | 12/2003 | Santini et al. |
| 6,699,281 B2 | 3/2004 | Vallana et al. |
| 6,730,064 B2 | 5/2004 | Ragheb et al. |
| 6,730,116 B1 | 5/2004 | Wolinsky et al. |
| 6,752,829 B2 | 6/2004 | Kocur et al. |
| 6,758,859 B1 | 7/2004 | Dang et al. |
| 6,764,507 B2 | 7/2004 | Shanley et al. |
| 6,774,278 B1 | 8/2004 | Ragheb et al. |
| 6,776,796 B2 | 8/2004 | Falotico et al. |
| 6,783,543 B2 | 8/2004 | Jang |
| 6,805,898 B1 | 10/2004 | Wu et al. |
| 6,808,536 B2 | 10/2004 | Wright et al. |
| 6,849,089 B2 | 2/2005 | Stoll |
| 6,852,123 B2 | 2/2005 | Brown |
| 6,855,125 B2 | 2/2005 | Shanley |
| 6,863,685 B2 | 3/2005 | Davila et al. |
| 6,869,443 B2 | 3/2005 | Buscemi et al. |
| 6,929,660 B1 | 8/2005 | Ainsworth et al. |
| 7,056,338 B2 | 6/2006 | Shanley et al. |
| 2001/0027291 A1 | 10/2001 | Shanley |
| 2001/0027340 A1 | 10/2001 | Wright et al. |
| 2001/0029351 A1 | 10/2001 | Falotico et al. |
| 2002/0007209 A1 | 1/2002 | De Scheerder et al. |
| 2002/0013619 A1 | 1/2002 | Shanley |
| 2002/0032414 A1 | 3/2002 | Ragheb et al. |
| 2002/0038145 A1 | 3/2002 | Jang |
| 2002/0038146 A1 | 3/2002 | Harry |
| 2002/0068969 A1 | 6/2002 | Shanley et al. |
| 2002/0082680 A1 | 6/2002 | Shanley et al. |
| 2002/0107563 A1 | 8/2002 | Shanley |
| 2002/0155212 A1 | 10/2002 | Hossainy |
| 2002/0165604 A1 | 11/2002 | Shanley |
| 2003/0009214 A1 | 1/2003 | Shanley |
| 2003/0028243 A1 | 2/2003 | Bates et al. |
| 2003/0028244 A1 | 2/2003 | Bates et al. |
| 2003/0036794 A1 | 2/2003 | Ragheb et al. |
| 2003/0060877 A1 | 3/2003 | Falotico et al. |
| 2003/0068355 A1 | 4/2003 | Shanley et al. |
| 2003/0100865 A1 | 5/2003 | Santini et al. |
| 2003/0105511 A1 | 6/2003 | Welsh et al. |
| 2001/0125803 | 7/2003 | Vallana et al. |
| 2003/0125803 A1 | 7/2003 | Vallana et al. |
| 2003/0167085 A1 | 9/2003 | Shanley |
| 2003/0176915 A1 | 9/2003 | Wright et al. |
| 2003/0199970 A1 | 10/2003 | Shanley |
| 2003/0216699 A1 | 11/2003 | Falotico |
| 2003/0225420 A1 | 12/2003 | Wardle |
| 2004/0006382 A1 | 1/2004 | Sohier |
| 2004/0024449 A1 | 2/2004 | Boyle |
| 2004/0093067 A1 | 5/2004 | Israel |
| 2004/0122505 A1 | 6/2004 | Shanley |
| 2004/0122506 A1 | 6/2004 | Shanley et al. |
| 2004/0127976 A1 | 7/2004 | Diaz |
| 2004/0127977 A1 | 7/2004 | Shanley |
| 2004/0142014 A1 | 7/2004 | Litvack et al. |
| 2004/0143321 A1 | 7/2004 | Litvack et al. |
| 2004/0143322 A1 | 7/2004 | Litvack et al. |
| 2004/0166140 A1 | 8/2004 | Santini et al. |
| 2004/0193255 A1 | 9/2004 | Shanley et al. |
| 2004/0202692 A1 | 10/2004 | Shanley et al. |
| 2004/0204756 A1 | 10/2004 | Diaz et al. |
| 2004/0220660 A1 | 11/2004 | Shanley et al. |
| 2004/0220665 A1 | 11/2004 | Hossainy et al. |
| 2004/0225350 A1 | 11/2004 | Shanley |
| 2004/0249449 A1 | 12/2004 | Shanley et al. |
| 2005/0058684 A1 | 3/2005 | Shanley et al. |
| 2005/0060020 A1 | 3/2005 | Jenson |
| 2005/0074545 A1 | 4/2005 | Thomas |
| 2005/0075714 A1 | 4/2005 | Cheng et al. |
| 2005/0100577 A1 | 5/2005 | Parker et al. |
| 2005/0119720 A1 | 6/2005 | Gale et al. |
| 2005/0137678 A1 | 6/2005 | Varma |
| 2005/0137683 A1 | 6/2005 | Hezi-Yamit et al. |
| 2005/0222676 A1 | 10/2005 | Shanley et al. |
| 2005/0234538 A1 | 10/2005 | Litvack et al. |
| 2005/0234544 A1 | 10/2005 | Shanley |
| 2005/0278016 A1 | 12/2005 | Welsh et al. |
| 2006/0008503 A1 | 1/2006 | Shanley |
| 2006/0009838 A1 | 1/2006 | Shanley et al. |
| 2006/0030931 A1 | 2/2006 | Shanley |
| 2006/0064157 A1 | 3/2006 | Shanley |
| 2006/0096660 A1 | 5/2006 | Diaz |
| 2006/0122688 A1 | 6/2006 | Shanley et al. |
| 2006/0122697 A1 | 6/2006 | Shanley et al. |
| 2006/0177564 A1 | 8/2006 | Diaz et al. |
| 2006/0178734 A1 | 8/2006 | Parker et al. |
| 2006/0178735 A1 | 8/2006 | Litvack et al. |

FOREIGN PATENT DOCUMENTS

| | | |
|---|---|---|
| EP | 0747069 | 12/1996 |
| EP | 770401 | 5/1997 |
| EP | 875218 | 4/1998 |
| EP | 950386 | 10/1999 |
| EP | 968013 | 1/2000 |
| EP | 1132058 | 9/2001 |
| EP | 1172074 | 1/2002 |
| EP | 1181903 | 2/2002 |
| EP | 1222941 | 7/2002 |
| EP | 1277449 | 1/2003 |
| EP | 1498084 | 1/2005 |
| EP | 1527754 | 5/2005 |
| EP | 1561436 | 8/2005 |

| | | |
|---|---|---|
| EP | 1582180 | 10/2005 |
| EP | 1600180 | 11/2005 |
| WO | WO-9306792 | 4/1993 |
| WO | WO-9823228 | 6/1998 |
| WO | WO-9836784 | 8/1998 |
| WO | WO-9916386 | 4/1999 |
| WO | WO-9923977 | 5/1999 |
| WO | WO-9949928 | 10/1999 |
| WO | WO-0010622 | 3/2000 |
| WO | WO-0117577 | 3/2001 |
| WO | WO-0226281 | 4/2002 |
| WO | WO-0232347 | 4/2002 |
| WO | WO-02060506 | 8/2002 |
| WO | WO-03015664 | 2/2003 |
| WO | WO-03077730 | 9/2003 |
| WO | WO-04043510 | 5/2004 |
| WO | WO-04043511 | 5/2004 |
| WO | WO-04087015 | 10/2004 |
| WO | WO-04096176 | 11/2004 |
| WO | WO-05004945 | 1/2005 |
| WO | WO-05027794 | 3/2005 |
| WO | WO-05046521 | 5/2005 |
| WO | WO-05053937 | 6/2005 |
| WO | WO-05102220 | 11/2005 |
| WO | WO-05115277 | 12/2005 |
| WO | WO-05120397 | 12/2005 |
| WO | WO-2005118971 | 12/2005 |
| WO | WO-06007473 | 1/2006 |
| WO | WO-06012034 | 2/2006 |
| WO | WO-06012060 | 2/2006 |

OTHER PUBLICATIONS

P.W. Serruys, et al., The Effect of Variale Dose and Release Kinetics on Neointimal Hyperplasia Using a Novel Raclitaxel-Eluting Stent Platform, Journal of the American College of Cardology, vol. 46, No. 2, 2005.

* cited by examiner 320, 420

EXPANDABLE MEDICAL DEVICE FOR DELIVERY OF BENEFICIAL AGENT

CROSS-REFERENCE TO RELATED APPLICATIONS

This application is a continuation-in-part of pending U.S. application Ser. No. 10/456,292, filed on Jun. 5, 2003 (pending), which is a continuation of U.S. application Ser. No. 09/688,092, filed on Oct. 16, 2000 now abandoned, which is a continuation-in-part of U.S. application Ser. No. 09/183,555, filed Oct. 29, 1998, now U.S. Pat. No. 6,241,762, which claims the benefit of Provisional Application Ser. No. 60/079,881, filed Mar. 30, 1998, each of which are incorporated herein by reference in their entirety.

BACKGROUND OF THE INVENTION

The present invention relates to tissue-supporting medical devices, and more particularly to expandable, non-removable devices that are implanted within a bodily lumen of a living animal or human to support the organ and maintain patency, and that can deliver a beneficial agent to the intervention site.

In the past, permanent or biodegradable devices have been developed for implantation within a body passageway to maintain patency of the passageway. These devices are typically introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

Known stent designs include monofilament wire coil stents (U.S. Pat. No. 4,969,458); welded metal cages (U.S. Pat. Nos. 4,733,665 and 4,776,337); and, most prominently, thin-walled metal cylinders with axial slots formed around the circumference (U.S. Pat. Nos. 4,733,665, 4,739,762, and 4,776,337). Known construction materials for use in stents include polymers, organic fabrics and biocompatible metals, such as, stainless steel, gold, silver, tantalum, titanium, and shape memory alloys such as Nitinol.

U.S. Pat. Nos. 4,733,665, 4,739,762, and 4,776,337 disclose expandable and deformable interluminal vascular grafts in the form of thin-walled tubular members with axial slots allowing the members to be expanded radially outwardly into contact with a body passageway. After insertion, the tubular members are mechanically expanded beyond their elastic limit and thus permanently fixed within the body. The force required to expand these tubular stents is proportional to the thickness of the wall material in a radial direction. To keep expansion forces within acceptable levels for use within the body (e.g., 5–10 atm), these designs must use very thin-walled materials (e.g., stainless steel tubing with 0.0025 inch thick walls). However, materials this thin are not visible on conventional fluoroscopic and x-ray equipment and it is therefore difficult to place the stents accurately or to find and retrieve stents that subsequently become dislodged and lost in the circulatory system.

Further, many of these thin-walled tubular stent designs employ networks of long, slender struts whose width in a circumferential direction is two or more times greater than their thickness in a radial direction. When expanded, these struts are frequently unstable, that is, they display a tendency to buckle, with individual struts twisting out of plane. Excessive protrusion of these twisted struts into the bloodstream has been observed to increase turbulence, and thus encourage thrombosis. Additional procedures have often been required to attempt to correct this problem of buckled struts. For example, after initial stent implantation is determined to have caused buckling of struts, a second, high-pressure balloon (e.g., 12 to 18 atm) would be used to attempt to drive the twisted struts further into the lumen wall. These secondary procedures can be dangerous to the patient due to the risk of collateral damage to the lumen wall.

Many of the known stents display a large elastic recovery, known in the field as "recoil," after expansion inside a lumen. Large recoil necessitates over-expansion of the stent during implantation to achieve the desired final diameter. Over-expansion is potentially destructive to the lumen tissue. Known stents of the type described above experience recoil of up to about 6 to 12% from maximum expansion.

Large recoil also makes it very difficult to securely crimp most known stents onto delivery catheter balloons. As a result, slippage of stents on balloons during interluminal transportation, final positioning, and implantation has been an ongoing problem. Many ancillary stent securing devices and techniques have been advanced to attempt to compensate for this basic design problem. Some of the stent securing devices include collars and sleeves used to secure the stent onto the balloon.

Another problem with known stent designs is non-uniformity in the geometry of the expanded stent. Non-uniform expansion can lead to non-uniform coverage of the lumen wall creating gaps in coverage and inadequate lumen support. Further, over expansion in some regions or cells of the stent can lead to excessive material strain and even failure of stent features. This problem is potentially worse in low expansion force stents having smaller feature widths and thicknesses in which manufacturing variations become proportionately more significant. In addition, a typical delivery catheter for use in expanding a stent includes a balloon folded into a compact shape for catheter insertion. The balloon is expanded by fluid pressure to unfold the balloon and deploy the stent. This process of unfolding the balloon causes uneven stresses to be applied to the stent during expansion of the balloon due to the folds causing the problem non-uniform stent expansion.

U.S. Pat. No. 5,545,210 discloses a thin-walled tubular stent geometrically similar to those discussed above, but constructed of a nickel-titanium shape memory alloy ("Nitinol"). This design permits the use of cylinders with thicker walls by making use of the lower yield stress and lower elastic modulus of martensitic phase Nitinol alloys. The expansion force required to expand a Nitinol stent is less than that of comparable thickness stainless steel stents of a conventional design. However, the "recoil" problem after expansion is significantly greater with Nitinol than with other materials. For example, recoil of a typical design Nitinol stent is about 9%. Nitinol is also more expensive, and more difficult to fabricate and machine than other stent materials, such as stainless steel.

All of the above stents share a critical design property: in each design, the features that undergo permanent deformation during stent expansion are prismatic, i.e., the cross sections of these features remain constant or change very gradually along their entire active length. To a first approximation, such features deform under transverse stress as simple beams with fixed or guided ends: essentially, the features act as a leaf springs. These leaf spring like structures are ideally suited to providing large amounts of elastic deformation before permanent deformation commences.

This is exactly the opposite of ideal stent behavior. Further, the force required to deflect prismatic stent struts in the circumferential direction during stent expansion is proportional to the square of the width of the strut in the circumferential direction. Expansion forces thus increase rapidly with strut width in the above stent designs. Typical expansion pressures required to expand known stents are between about 5 and 10 atmospheres. These forces can cause substantial damage to tissue if misapplied.

In addition to the above-mentioned risks to a patient, restenosis is a major complication which can arise following the implantation of stents, using stent devices such as those described above, and other vascular interventions such as angioplasty. Simply defined, restenosis is a wound healing process that reduces the vessel lumen diameter by scar tissue formation and which may ultimately result in reocclusion of the lumen. Despite the introduction of improved surgical techniques, devices and pharmaceutical agents, the overall restenosis rate is still reported in the range of 25% to 50% within six to twelve months after an angioplasty procedure. To correct this problem, additional revascularization procedures are frequently required, thereby increasing trauma and risk to the patient.

Several techniques under development to address the problem of restenosis are irradiation of the injury site and the use of stents to deliver a variety of beneficial or pharmaceutical agents to the traumatized vessel lumen. In the latter case, a stent is frequently surface-coated with a beneficial agent (often a drug-impregnated polymer) and implanted at the angioplasty site. Alternatively, an external drug-impregnated polymer sheath is mounted over the stent and co-deployed in the vessel. In either case, it has proven difficult to deliver a sufficient amount of beneficial agent to the trauma site so as to satisfactorily prevent the growth of scar tissue and thereby reduce the likelihood of restenosis. Even with relatively thick coatings of the beneficial agent or sheaths of increased thickness surrounding the stents, restenosis has been found to occur. Furthermore, increasing the effective stent thickness (e.g., by providing increased coatings of the beneficial agent) is undesirable for a number of reasons, including increased trauma to the vessel lumen during implantation and reduced flow cross-section of the lumen after implantation. Moreover, coating thickness is one of several factors that affect the release kinetics of the beneficial agent, and limitations on thickness thereby limit the range of release rates, durations, and the like that can be achieved.

SUMMARY OF THE INVENTION

In view of the drawbacks of the prior art, it would be advantageous to provide a stent capable of delivering a relatively large volume of a beneficial agent to a traumatized site in a vessel lumen without increasing the effective wall thickness of the stent, and without adversely impacting the mechanical expansion properties of the stent.

In accordance with one aspect of the invention, an expandable medical device includes at least one cylindrical tube; a plurality of substantially rigid sections interconnected to form the at least one cylindrical tube; a plurality of ductile hinges formed between the substantially rigid sections, the ductile hinges allowing the cylindrical tube to be expanded or compressed from a first diameter to a second diameter by deformation of the ductile hinges without substantial deformation of the substantially rigid sections; and a plurality of beneficial agent containing openings in the plurality of substantially rigid sections.

In accordance with a further aspect of the present invention, an expandable stent includes a plurality of substantially rigid sections; a plurality of ductile hinges interconnecting the plurality of substantially rigid sections to form a cylindrical stent which is expandable from a first diameter to a second diameter by deformation of the plurality of ductile hinges without substantial deformation of the substantially rigid sections; and a plurality of openings containing a beneficial agent, the openings positioned in the substantially rigid sections.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE PREFERRED EMBODIMENTS

Figure 1:
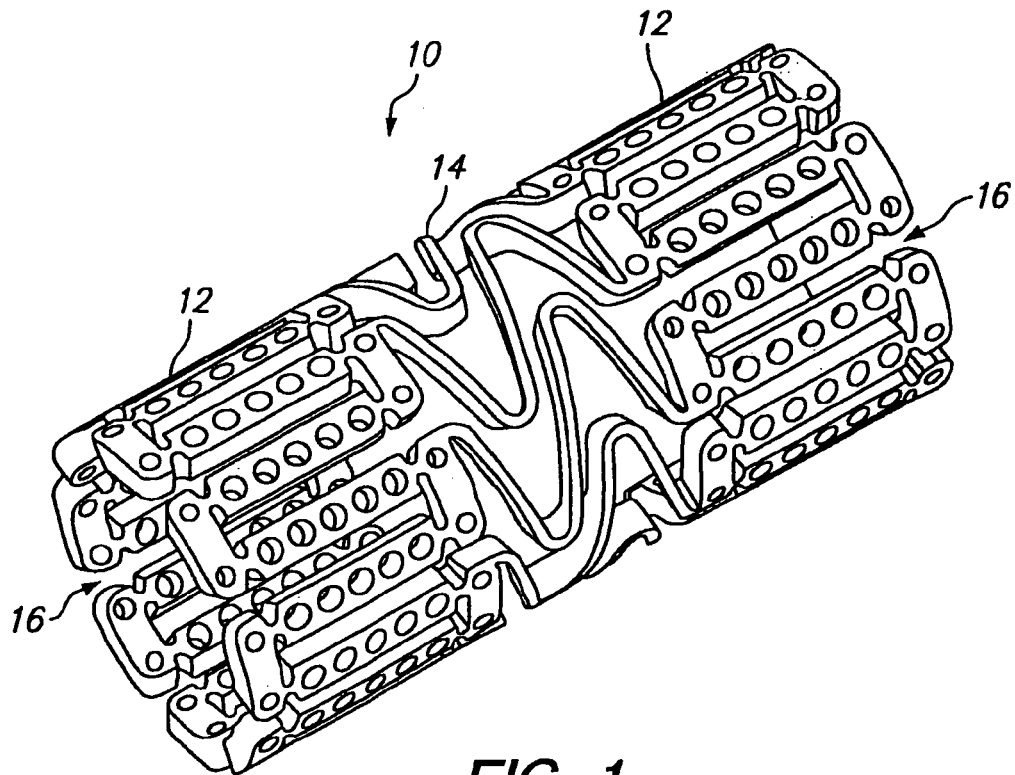
FIG. 1 is a perspective view of a tissue-supporting device in accordance with a first preferred embodiment of the present invention.
Figure 2:
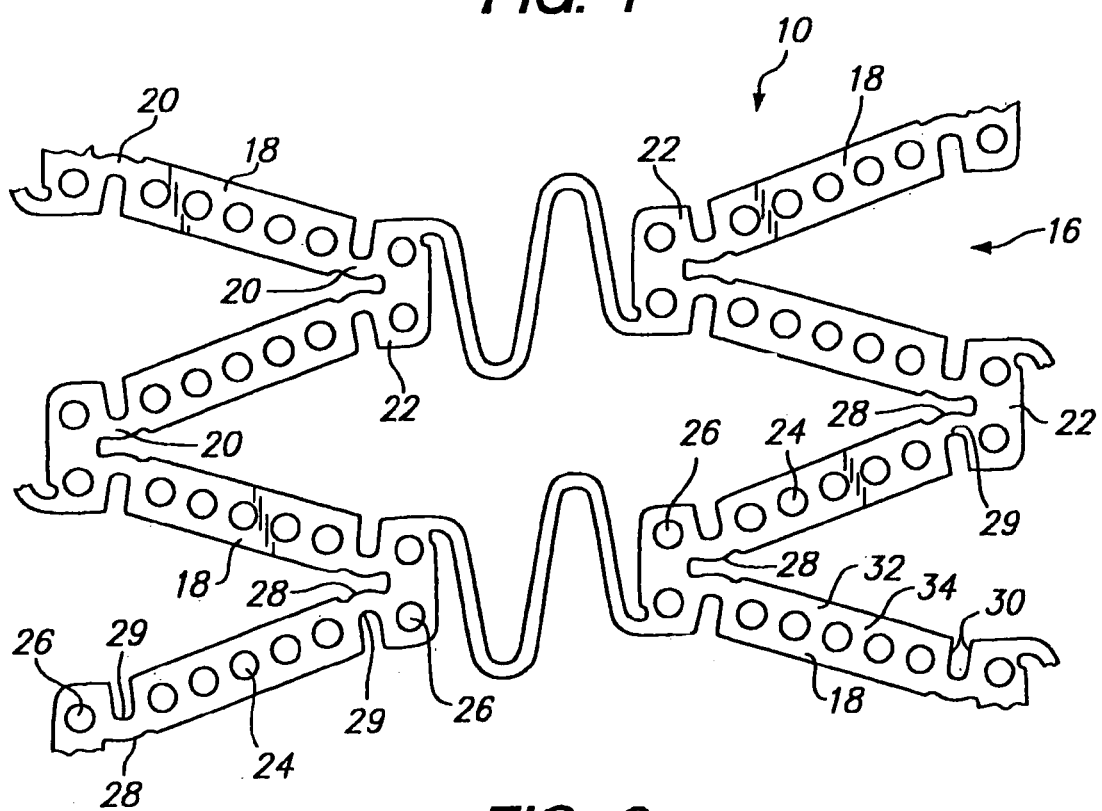
FIG. 2 is an enlarged side view of a portion thereof.

Referring to FIGS. 1 and 2, a tissue supporting device in accordance with a preferred embodiment of the present invention is shown generally by reference numeral 10. The tissue supporting device 10 includes a plurality of cylindrical tubes 12 connected by S-shaped bridging elements 14. The bridging elements 14 allow the tissue supporting device to bend axially when passing through the tortuous path of the vasculature to the deployment site and allow the device to bend when necessary to match the curvature of a lumen to be supported. The S-shaped bridging elements 14 provide improved axial flexibility over prior art devices due to the thickness of the elements in the radial direction which allows the width of the elements to be relatively small without sacrificing radial strength. For example, the width of the bridging elements 14 may be about 0.0015–0.0018 inches (0.0381–0.0457 mm). Each of the cylindrical tubes 12 has a plurality of axial slots 16 extending from an end surface of the cylindrical tube toward an opposite end surface.

Formed between the slots 16 is a network of axial struts 18 and links 22. The cross section (and rectangular moment of inertia) of each of the struts 18 is preferably not constant along the length of the strut. Rather, the strut cross section changes abruptly at both ends of each strut 18 adjoining the links 22. The preferred struts 18 are thus not prismatic. Each individual strut 18 is preferably linked to the rest of the structure through a pair of reduced sections 20, one at each end, which act as stress/strain concentration features. The reduced sections 20 of the struts function as hinges in the cylindrical structure. Since the stress/strain concentration features are designed to operate into the plastic deformation range of generally ductile materials, they are referred to as ductile hinges 20. Such features are also commonly referred to as "Notch Hinges" or "Notch Springs" in ultra-precision mechanism design, where they are used exclusively in the elastic range.

With reference to the drawings and the discussion, the width of any feature is defined as its dimension in the circumferential direction of the cylinder. The length of any feature is defined as its dimension in the axial direction of the cylinder. The thickness of any feature is defined as the wall thickness of the cylinder.

Ductile hinges 20 are preferably asymmetric ductile hinges that produce different strain versus deflection-angle functions in expansion and compression. Each of the ductile hinges 20 is formed between a arc surface 28 and a concave notch surface 29. The ductile hinge 20 according to a preferred embodiment essentially takes the form of a small, prismatic curved beam having a substantially constant cross section. However, a thickness of the curved ductile hinge 20 may vary somewhat as long as the ductile hinge width remains constant along a portion of the hinge length. The width of the curved beam is measure along the radius of curvature of the beam. This small curved beam is oriented such that the smaller concave notch surface 29 is placed in tension in the device crimping direction, while the larger arc surface 28 of the ductile hinges is placed in tension in the device expansion direction. Again, there is no local minimum width of the ductile hinge 20 along the (curved) ductile hinge axis, and no concentration of material strain. During device expansion tensile strain will be distributed along the arc surface 28 of the hinge 20 and maximum expansion will be limited by the angle of the walls of the concave notch 29 which provide a geometric deflection limiting feature. The notches 29 each have two opposed angled walls 30 which function as a stop to limit geometric deflection of the ductile hinge, and thus limit maximum device expansion. As the cylindrical tubes 12 are expanded and bending occurs at the ductile hinges 20, the angled side walls 30 of the notches 29 move toward each other. Once the opposite side walls 30 of a notch come into contact with each other, they resist further expansion of the particular ductile hinge causing further expansion to occur at other sections of the tissue supporting device. This geometric deflection limiting feature is particularly useful where uneven expansion is caused by either variations in the tissue supporting device 10 due to manufacturing tolerances or uneven balloon expansion. Maximum tensile strain can therefore be reliably limited by adjusting the initial length of the arc shaped ductile hinge 20 over which the total elongation is distributed.

The presence of the ductile hinges 20 allows all of the remaining features in the tissue supporting device to be increased in width or the circumferentially oriented component of their respective rectangular moments of inertia— thus greatly increasing the strength and rigidity of these features. The net result is that elastic, and then plastic deformation commence and propagate in the ductile hinges 20 before other structural elements of the device undergo any significant elastic deformation. The force required to expand the tissue supporting device 10 becomes a function of the geometry of the ductile hinges 20, rather than the device structure as a whole, and arbitrarily small expansion forces can be specified by changing hinge geometry for virtually any material wall thickness. In particular, wall thicknesses great enough to be visible on a fluoroscope can be chosen for any material of interest.

In order to get minimum recoil, the ductile hinges 20 should be designed to operate well into the plastic range of the material, and relatively high local strain-curvatures are developed. When these conditions apply, elastic curvature is a very small fraction of plastic or total curvature, and thus when expansion forces are relaxed, the percent change in hinge curvature is very small. When incorporated into a strut network designed to take maximum advantage of this effect, the elastic springback, or "recoil," of the overall stent structure is minimized.

In the preferred embodiment of FIGS. 1 and 2, it is desirable to increase the width of the individual struts 18 between the ductile hinges 20 to the maximum width that is geometrically possible for a given diameter and a given number of struts arrayed around that diameter. The only geometric limitation on strut width is the minimum practical width of the slots 16 which is about 0.002 inches (0.0508 mm) for laser machining. Lateral stiffness of the struts 18 increases as the cube of strut width, so that relatively small increases in strut width significantly increase strut stiffness. The net result of inserting ductile hinges 20 and increasing strut width is that the struts 18 no longer act as flexible leaf springs, but act as essentially rigid beams between the ductile hinges. All radial expansion or compression of the cylindrical tissue supporting device 10 is accommodated by mechanical strain in the hinge features 20, and yield in the hinge commences at very small overall radial expansion or compression.

Yield in ductile hinges at very low gross radial deflections also provides the superior crimping properties displayed by the ductile hinge-based designs. When a tissue supporting device is crimped onto a folded catheter balloon, very little radial compression of the device is possible since the initial fit between balloon and device is already snug. Most stents simply rebound elastically after such compression, resulting in very low clamping forces and the attendant tendency for the stent to slip on the balloon. Ductile hinges, however, sustain significant plastic deformation even at the low deflections occurring during crimping onto the balloon, and therefore a device employing ductile hinges displays much higher clamping forces. The ductile hinge designs according to the present invention may be securely crimped onto a balloon of a delivery catheter by hand or by machine without the need for auxiliary retaining devices commonly used to hold known stents in place.

The ductile hinge 20 illustrated in FIGS. 1 and 2 is exemplary of a preferred structure that will function as a stress/strain concentrator. Many other stress/strain concentrator configurations may also be used as the ductile hinges in the present invention, as shown and described for example in U.S. Pat. No. 6,241,762, the entire contents of which is hereby incorporated by reference. The geometric details of the stress/strain concentration features or ductile hinges 20 can be varied greatly to tailor the exact mechanical expansion properties to those required in a specific application. The ductile hinges according to the present invention generally include an abrupt change in width of a strut that functions to concentrate stresses and strains in the narrower section of the strut. These ductile hinges also generally include features to limit mechanical deflection of attached struts and features to control material strain during large strut deflections. Although the ductile hinges have been illustrated in FIG. 2 as positioned along the length of the struts 18 and the links 22, they may also be positioned at other locations in other designs without departing from the present invention.

At intervals along the neutral axis of the struts 18, at least one and more preferably a series of through-openings 24 are formed by laser drilling or any other means known to one skilled in the art. Similarly, at least one and preferably a series of through-openings 26 are formed at selected locations in the links 22. Although the use of through-openings 24 and 26 in both the struts 18 and links 22 is preferred, it should be clear to one skilled in the art that through-openings could be formed in only one of the struts and links. In the illustrated embodiment, the through-openings 24, 26 are circular in nature and thereby form cylindrical holes extending through the width of the tissue supporting device 10. It should be apparent to one skilled in the art, however, that through-openings of any geometrical shape or configuration could of course be used without departing from the scope of the present invention.

The behavior of the struts 18 in bending is analogous to the behavior of an I-beam or truss. The outer edge elements 32 of the struts 18 correspond to the I-beam flange and carry the tensile and compressive stresses, whereas the inner elements 34 of the struts 18 correspond to the web of an I-beam which carries the shear and helps to prevent buckling and wrinkling of the faces. Since most of the bending load is carried by the outer edge elements 32 of the struts 18, a concentration of as much material as possible away from the neutral axis results in the most efficient sections for resisting strut flexure. As a result, material can be judiciously removed along the axis of the strut so as to form through-openings 24, 26 without adversely impacting the strength and rigidity of the strut. Since the struts 18 and links 22 thus formed remain essentially rigid during stent expansion, the through-openings 24, 26 are also non-deforming.

The through-openings 24, 26 in the struts 18 promote the healing of the intervention site by promoting regrowth of the endothelial cells. By providing the through-openings 24, 26 in the struts, 18, the cross section of the strut is effectively reduced without decreasing the strength and integrity of the strut, as described above. As a result, the overall distance across which endothelial cell regrowth must occur is also reduced to approximately 0.0025–0.0035 inches, which is approximately one-half of the thickness of a convention stent. It is further believed that during insertion of the expandable medical device, cells from the endothelial layer may be scraped from the inner wall of the lumen by the through-openings 24, 26 and remain therein after implantation. The presence of such endothelial cells thus provide a basis for the healing of the lumen.

The through-openings 24, 26 may also be loaded with an agent, most preferably a beneficial agent, such as a drug in a biocompatible matrix, for delivery to the lumen in which the tissue support device 10 is deployed.

The terms "drug" and "therapeutic agent" are used interchangeably to refer to any therapeutically active substance that is delivered to a living being to produce a desired, usually beneficial, effect.

The term "matrix" or "biocompatible matrix" are used interchangeably to refer to a medium or material that, upon implantation in a subject, does not elicit a detrimental response sufficient to result in the rejection of the matrix. The matrix may contain or surround a therapeutic agent, and/or modulate the release of the therapeutic agent into the body. A matrix is also a medium that may simply provide support, structural integrity or structural barriers. The matrix may be polymeric, non-polymeric, hydrophobic, hydrophilic, lipophilic, amphiphilic, and the like. The matrix may be bioresorbable or non-bioresorbable.

The term "bioresorbable" refers to a material, as defined herein, that can be broken down by either chemical or physical process, upon interaction with a physiological environment. The matrix can erode or dissolve. A bioresorbable matrix serves a temporary function in the body, such as drug delivery, and is then degraded or broken into components that are metabolizable or excretable, over a period of time from minutes to years, preferably less than one year, while maintaining any requisite structural integrity in that same time period.

The term "openings" includes both through openings and recesses.

The term "polymer" refers to molecules formed from the chemical union of two or more repeating units, called monomers. Accordingly, included within the term "polymer" may be, for example, dimers, trimers and oligomers. The polymer may be synthetic, naturally-occurring or semi-synthetic. In preferred form, the term "polymer" refers to molecules which typically have a Mw greater than about 3000 and preferably greater than about 10,000 and a Mw that is less than about 10 million, preferably less than about a million and more preferably less than about 200,000. Examples of polymers include but are not limited to, poly-α-hydroxy acid esters such as, polylactic acid (PLLA or DLPLA), polyglycolic acid, polylactic-co-glycolic acid (PLGA), polylactic acid-co-caprolactone; poly (block-ethylene oxide-block-lactide-co-glycolide) polymers (PEO-block-PLGA and PEO-block-PLGA-block-PEO); polyethylene glycol and polyethylene oxide, poly (block-ethylene oxide-block-propylene oxide-block-ethylene oxide); polyvinyl pyrrolidone; polyorthoesters; polysaccharides and polysaccharide derivatives such as polyhyaluronic acid, poly (glucose), polyalginic acid, chitin, chitosan, chitosan derivatives, cellulose, methyl cellulose, hydroxyethylcellulose, hydroxypropylcellulose, carboxymethylcellulose, cyclodextrins and substituted cyclodextrins, such as beta-cyclodextrin sulfobutyl ethers; polypeptides and proteins, such as polylysine, polyglutamic acid, albumin; polyanhydrides; polyhydroxy alkonoates such as polyhydroxy valerate, polyhydroxy butyrate, and the like.

The embodiment of the invention shown in FIGS. 1 and 2 can be further refined by using Finite Element Analysis and other techniques to optimize the deployment of the beneficial agent within the through-openings of the struts and links. Basically, the shape and location of the through-openings 24, 26 can be modified to maximize the volume of the voids while preserving the relatively high strength and rigidity of the struts 18 with respect to the ductile hinges 20.

Figure 3:
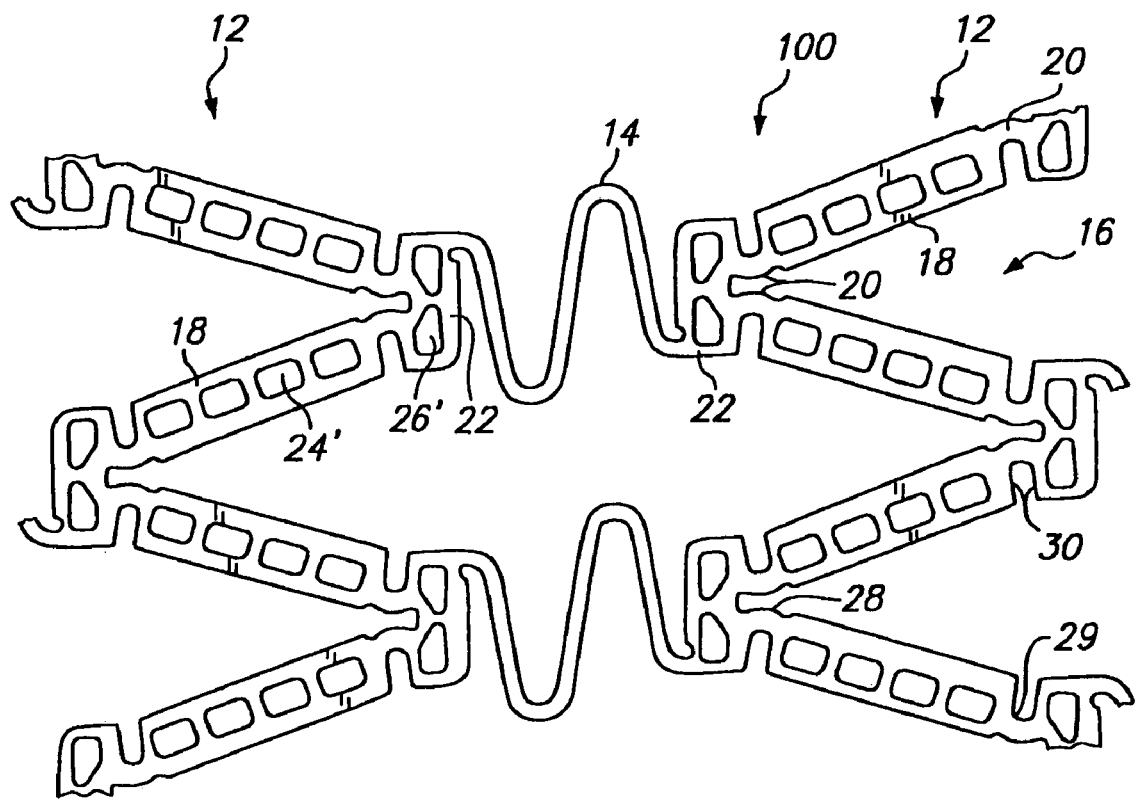
FIG. 3 is an enlarged side view of a tissue-supporting device in accordance with a further preferred embodiment of the present invention.

FIG. 3 illustrates a further preferred embodiment of the present invention, wherein like reference numerals have been used to indicate like components. The tissue supporting device 100 includes a plurality of cylindrical tubes 12 connected by S-shaped bridging elements 14. Each of the cylindrical tubes 12 has a plurality of axial slots 16 extending from an end surface of the cylindrical tube toward an opposite end surface. Formed between the slots 16 is a network of axial struts 18 and links 22. Each individual strut 18 is linked to the rest of the structure through a pair of ductile hinges 20, one at each end, which act as stress/strain concentration features. Each of the ductile hinges 20 is formed between an arc surface 28 and a concave notch surface 29. The notches 29 each have two opposed angled walls 30 which function as a stop to limit geometric deflection of the ductile hinge, and thus limit maximum device expansion.

At intervals along the neutral axis of the struts 18, at least one and more preferably a series of through-openings 24' are formed by laser drilling or any other means known to one skilled in the art. Similarly, at least one and preferably a series of through-openings 26' are formed at selected locations in the links 22. Although the use of through-openings 24' and 26' in both the struts 18 and links 22 is preferred, it should be clear to one skilled in the art that through-openings could be formed in only one of the struts and links. In the illustrated embodiment, the through-openings 24' in the struts 18 are generally rectangular whereas the through-openings 26' in the links 22 are polygonal. It should be apparent to one skilled in the art, however, that through-openings of any geometrical shape or configuration could of course be used, and that the shape of through-openings 24, 24' may be the same or different from the shape of through-openings 26, 26', without departing from the scope of the present invention. As described in detail above, the through-openings 24', 26' may be loaded with an agent, most preferably a beneficial agent, for delivery to the lumen in which the tissue support device 100 is deployed.

The relatively large, protected through-openings 24, 24', 26, 26', as described above, make the expandable medical device of the present invention particularly suitable for delivering agents having more esoteric larger molecules or genetic or cellular agents, such as, for example, protein/enzymes, antibodies, antisense, ribozymes, gene/vector constructs, and cells (including but not limited to cultures of a patient's own endothelial cells). Many of these types of agents are biodegradable or fragile, have a very short or no shelf life, must be prepared at the time of use, or cannot be pre-loaded into delivery devices such as stents during the manufacture thereof for some other reason. The large through-openings in the expandable device of the present invention form protected areas or receptors to facilitate the loading of such an agent at the time of use, and to protect the agent from abrasion and extrusion during delivery and implantation.

Figure 4:
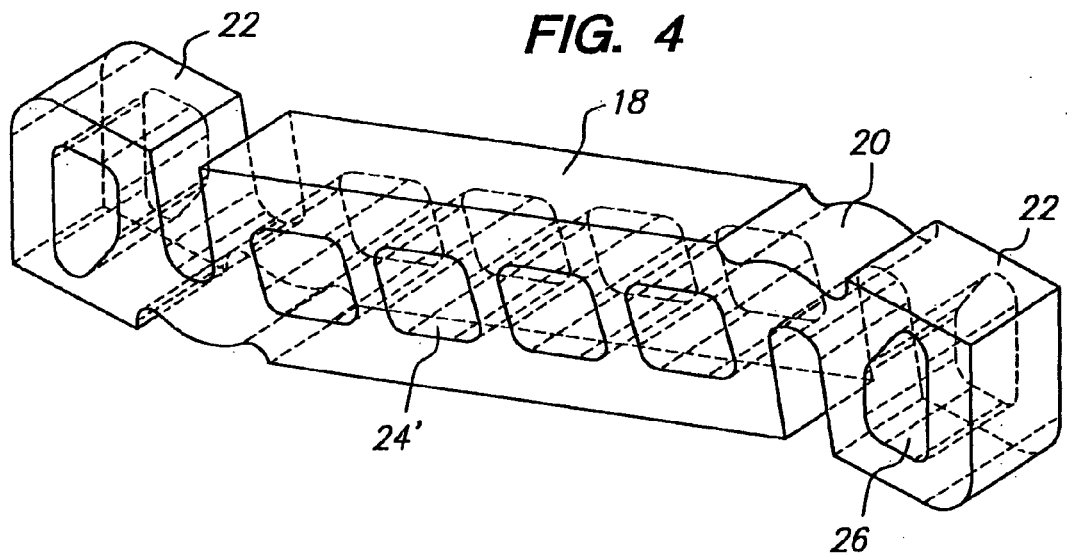
FIG. 4 is an enlarged side view of a portion of the stent shown in the device of FIG. 3.
Figure 5:
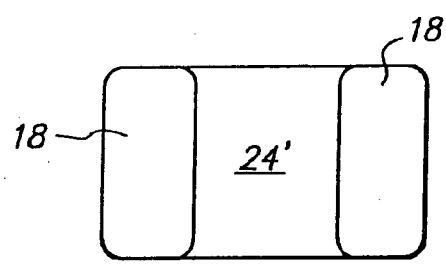
FIG. 5 is an enlarged cross section of an opening thereof.
Figure 6:
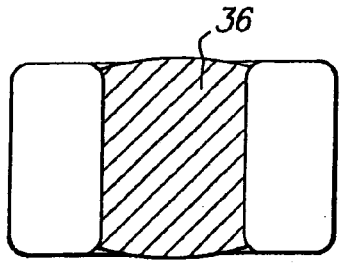
FIG. 6 is an enlarged cross section of an opening thereof illustrating beneficial agent loaded into the opening.
Figure 7:
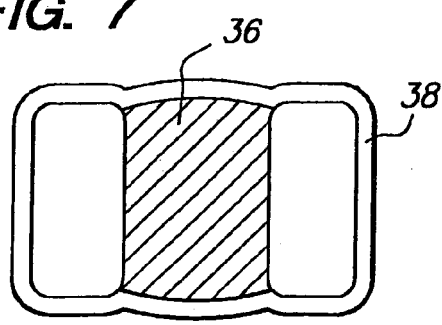
FIG. 7 is an enlarged cross section of an opening thereof illustrating a beneficial agent loaded into the opening and a thin coating of a beneficial agent.
Figure 8:
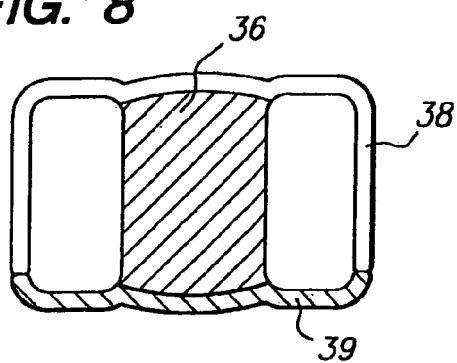
FIG. 8 is an enlarged cross section of an opening thereof illustrating a beneficial agent loaded into the opening and thin coatings of different beneficial agents on different surfaces of the device.

FIG. 4 shows an enlarged view of one of the struts 18 of device 100 disposed between a pair of ductile hinges 20. FIG. 5 illustrates a cross section of one of the openings 24' shown in FIG. 4. FIG. 6 illustrates the same cross section when a beneficial agent 36 has been loaded into the through-openings 24' of the struts 18. Optionally, after loading the through-openings 24' and/or the through-openings 26' with a beneficial agent 36, the entire exterior surface of the stent can be coated with a thin layer of a beneficial agent 38, which may be the same as or different from the beneficial agent 36, as schematically shown in FIG. 7. Still further, another variation of the present invention would coat the outwardly facing surfaces of the stent with a first beneficial agent 38 while coating the inwardly facing surfaces of the stent with a different beneficial agent 39, as illustrated in FIG. 8. The inwardly facing surface of the stent would be defined by at least the surfaces of the stent which, after expansion, forms the inner lumen passage. The outwardly facing surface of the stent would be defined by at least the surface of the stent which, after expansion, is in contact with and directly supports the inner wall of the lumen.

Figure 9:
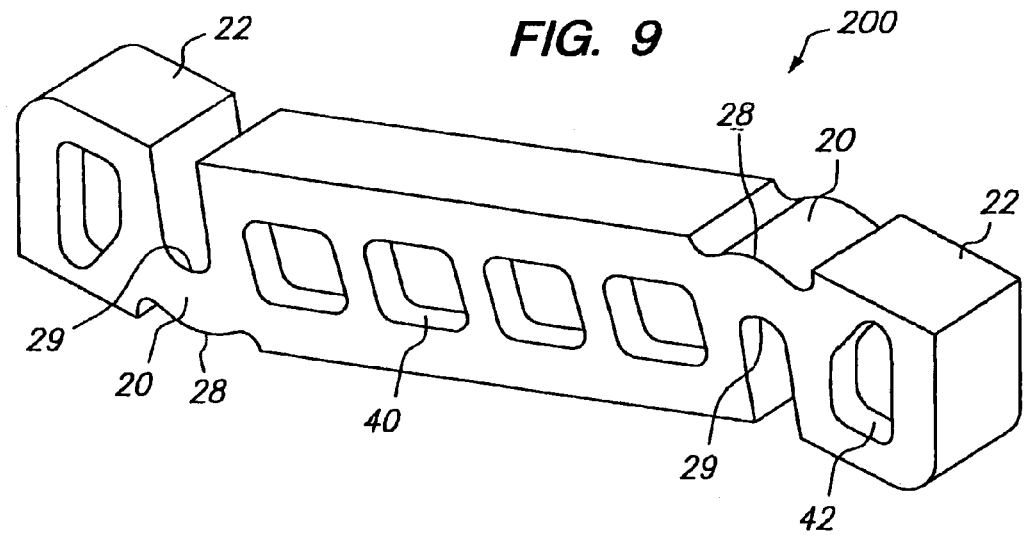
FIG. 9 is an enlarged side view of a portion of a stent in accordance with yet another preferred embodiment of the present invention.

FIG. 9 illustrates yet another preferred embodiment of the present invention, wherein like reference numerals have been used to indicate like components. Unlike the stents 10, 100 described above, tissue supporting device 200 does not include through-openings which extend through the entire width of the stent. Rather, the struts 18 and/or links 22 of stent 200 preferably include at least one and preferably a plurality of recesses 40, 42, formed respectively therein on one or both side surfaces of the stent 200. The recesses 40, 42, also defined as openings, indentations, grooves, and the like, are sufficiently sized so as to promote healing of the endothelial layer and to enable a beneficial agent 36 to be loaded therein. Recesses 40, 42, like through-holes 24, 24', 26, 26', may be formed in struts 18 without compromising the strength and rigidity thereof for the same reasons as noted above. As shown above in FIGS. 7 and 8, a surface coating of one or more beneficial agents may also be provided on stent 200.

The tissue supporting device 10, 100, 200 according to the present invention may be formed of any ductile material, such as steel, gold, silver, tantalum, titanium, Nitinol, other shape memory alloys, other metals, or even some plastics. One preferred method for making the tissue supporting device 10, 100, 200 involves forming a cylindrical tube 12 and then laser cutting the slots 16, notches 29 and through-openings 24, 24', 26, 26' or recesses 40, 42 into the tube. Alternatively, the tissue supporting device may be formed by electromachining, chemical etching followed by rolling and welding, or any other method known to one skilled in the art.

The design and analysis of stress/strain concentration for ductile hinges, and stress/strain concentration features in general, is complex. The stress concentration factor can be calculated for simple ductile hinge geometries, but is generally useful only in the linear elastic range. Stress concentration patterns for a number of other geometries can be determined through photoelastic measurements and other experimental methods. Stent designs based on the use of stress/strain concentration features, or ductile hinges, generally involve more complex hinge geometries and operate in the non-linear elastic and plastic deformation regimes.

Figure 10A:
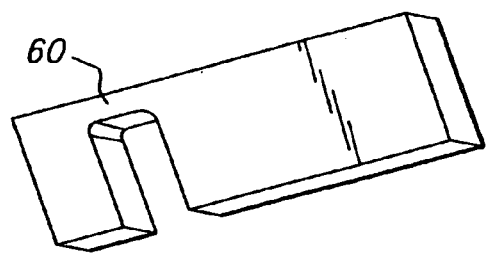
FIGS. 10a–10c are perspective, side, and cross-sectional views of an idealized ductile hinge for purposes of analysis.
Figure 10B:
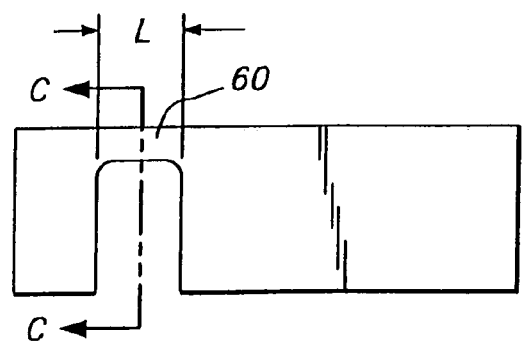
Figure 10C:
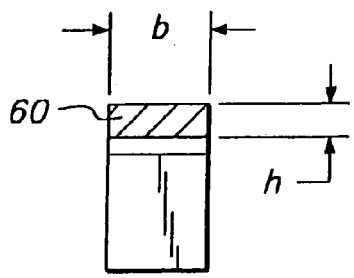
Figure 10D:
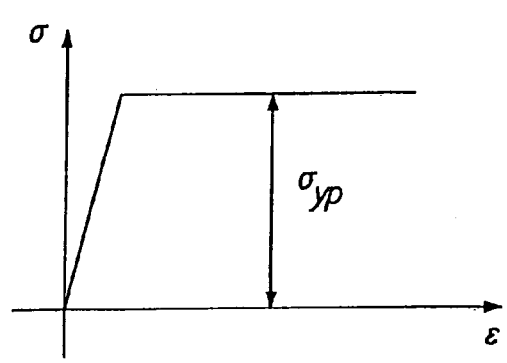
FIG. 10d is a stress/strain curve for the idealized ductile hinge.

The general nature of the relationship among applied forces, material properties, and ductile hinge geometry can be more easily understood through analysis of an idealized hinge 60 as shown in FIGS. 10a–10c. The hinge 60 is a simple beam of rectangular cross section having a width h, length L and thickness b. The idealized hinge 60 has elastic-ideally-plastic material properties which are characterized by the ideal stress/strain curve of FIG. 10d. It can be shown that the "plastic" or "ultimate bending moment" for such a beam is given by the expression:

$$M_p \equiv M_{ult} = \delta_{yp} \frac{bh^2}{4}$$

Where b corresponds to the cylindrical tube wall thickness, h is the circumferential width of the ductile hinge, and $\delta_{yp}$ is the yield stress of the hinge material. Assuming only that expansion pressure is proportional to the plastic moment, it can be seen that the required expansion pressure to expand the tissue supporting device increases linearly with wall thickness b and as the square of ductile hinge width h. It is thus possible to compensate for relatively large changes in wall thickness b with relatively small changes in hinge width h. While the above idealized case is only approximate, empirical measurements of expansion forces for different hinge widths in several different ductile hinge geometries have confirmed the general form of this relationship. Accordingly, for different ductile hinge geometries it is possible to increase the thickness of the tissue supporting device to achieve radiopacity while compensating for the increased thickness with a much smaller decrease in hinge width.

Ideally, the stent wall thickness b should be as thin as possible while still providing good visibility on a fluoroscope. For most stent materials, including stainless steel, this would suggest a thickness of about 0.005–0.007 inches (0.127–0.178 mm) or greater. Other materials which can be used to design the tissue supporting devices of the present invention include cobalt chromium alloys and other metal alloys, plastics, and bioresorbable materials with the hinge dimensions and shapes depending on the properties of the materials.

The inclusion of ductile hinges in a stent design can lower expansion forces/pressures to very low levels for any material thickness of interest. Thus ductile hinges allow the construction of optimal wall thickness tissue supporting devices at expansion force levels significantly lower than current non-visible designs.

The expansion forces required to expand the tissue supporting device 10, 100, 200 according to the present invention from an initial condition illustrated in FIG. 1 to an expanded condition is between 1 and 5 atmospheres, preferably between 2 and 3 atmospheres. The expansion may be performed in a known manner, such as by inflation of a balloon or by a mandrel. The tissue supporting device 10, 100, 200 in the expanded condition has a diameter which is preferably up to three times the diameter of the device in the initial unexpanded condition.

Figure 11:
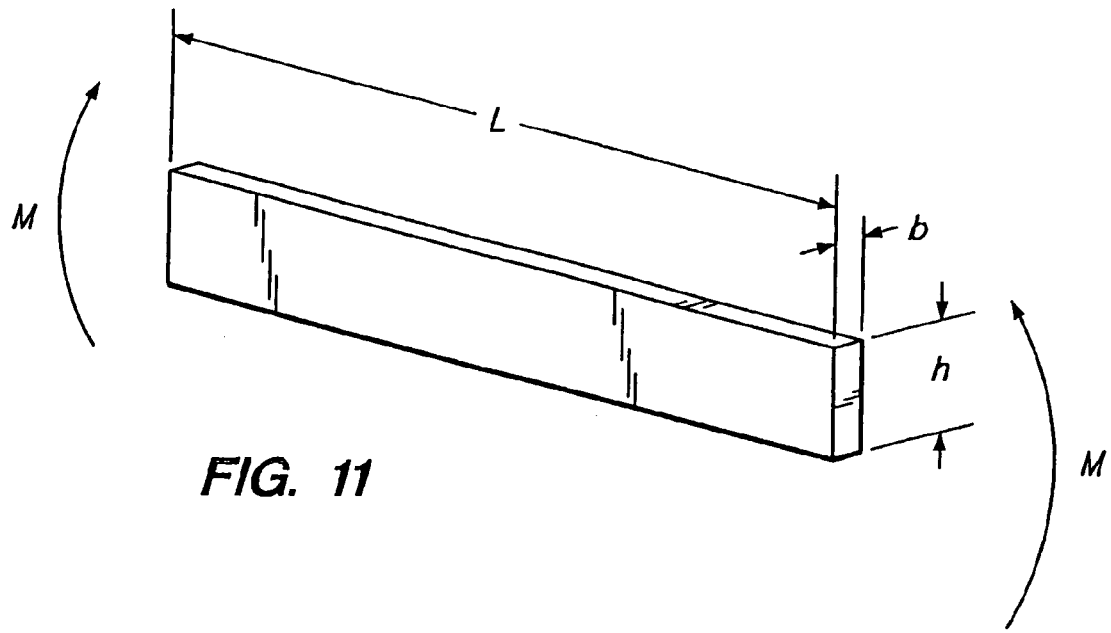
FIGS. 11 is a perspective view of a simple beam for purposes of calculation.

Many tissue supporting devices fashioned from cylindrical tubes comprise networks of long, narrow, prismatic beams of essentially rectangular cross section as shown in FIG. 11. These beams which make up the known tissue supporting devices may be straight or curved, depending on the particular design. Known expandable tissue supporting devices have a typical wall thickness b of 0.0025 inches (0.0635 mm), and a typical strut width h of 0.005 to 0.006 inches (0.127–0.1524 mm). The ratio of b:h for most known designs is 1:2 or lower. As b decreases and as the beam length L increases, the beam is increasingly likely to respond to an applied bending moment M by buckling, and many designs of the prior art have displayed this behavior. This can be seen in the following expression for the "critical buckling moment" for the beam of FIG. 6.

$$M_{crit} = \frac{\pi b^3 h \sqrt{EG(1 - 0.63 b/h)}}{6L}$$

Where: E=Modulus of Elasticity
G=Shear Modulus

By contrast, in a ductile hinge based design according to the present invention, only the hinge itself deforms during expansion. The typical ductile hinge 20 is not a long narrow beam as are the struts in the known stents. Wall thickness of the present invention may be increased to 0.005 inches (0.127 mm) or greater, while hinge width is typically 0.002–0.003 inches (0.0508–0.0762 mm), preferably 0.0025 inches (0.0635 mm) or less. Typical hinge length, at 0.002 to 0.005 inches (0.0508–0.0127 mm), is more than an order of magnitude less than typical strut length. Thus, the ratio of b:h in a typical ductile hinge 20 is 2:1 or greater. This is an inherently stable ratio, meaning that the plastic moment for such a ductile hinge beam is much lower than the critical buckling moment $M_{crit}$, and the ductile hinge beam deforms through normal strain-curvature. Ductile hinges 20 are thus not vulnerable to buckling when subjected to bending moments during expansion of the tissue supporting device 10, 100, 200.

To provide optimal recoil and crush-strength properties, it is desirable to design the ductile hinges so that relatively large strains, and thus large curvatures, are imparted to the hinge during expansion of the tissue supporting device. Curvature is defined as the reciprocal of the radius of curvature of the neutral axis of a beam in pure bending. A larger curvature during expansion results in the elastic curvature of the hinge being a small fraction of the total hinge curvature. Thus, the gross elastic recoil of the tissue supporting device is a small fraction of the total change in circumference. It is generally possible to do this because common stent materials, such as 316L Stainless Steel have very large elongations-to-failure (i.e., they are very ductile).

It is not practical to derive exact expressions for residual curvatures for complex hinge geometries and real materials (i.e., materials with non-idealized stress/strain curves). The general nature of residual curvatures and recoil of a ductile hinge may be understood by examining the moment-curvature relationship for the elastic-ideally-plastic rectangular hinge 60 shown in FIGS. 10a–c. It may be shown that the relationship between the applied moment and the resulting beam curvature is:

$$M = M_P \left[1 - \frac{1}{3}\left(\frac{y_O}{h/2}\right)^2\right] = 3/2 M_{yp} \left[1 - \frac{1}{3}\left(\frac{\kappa_{yp}}{\kappa}\right)^2\right]$$

Figure 12:
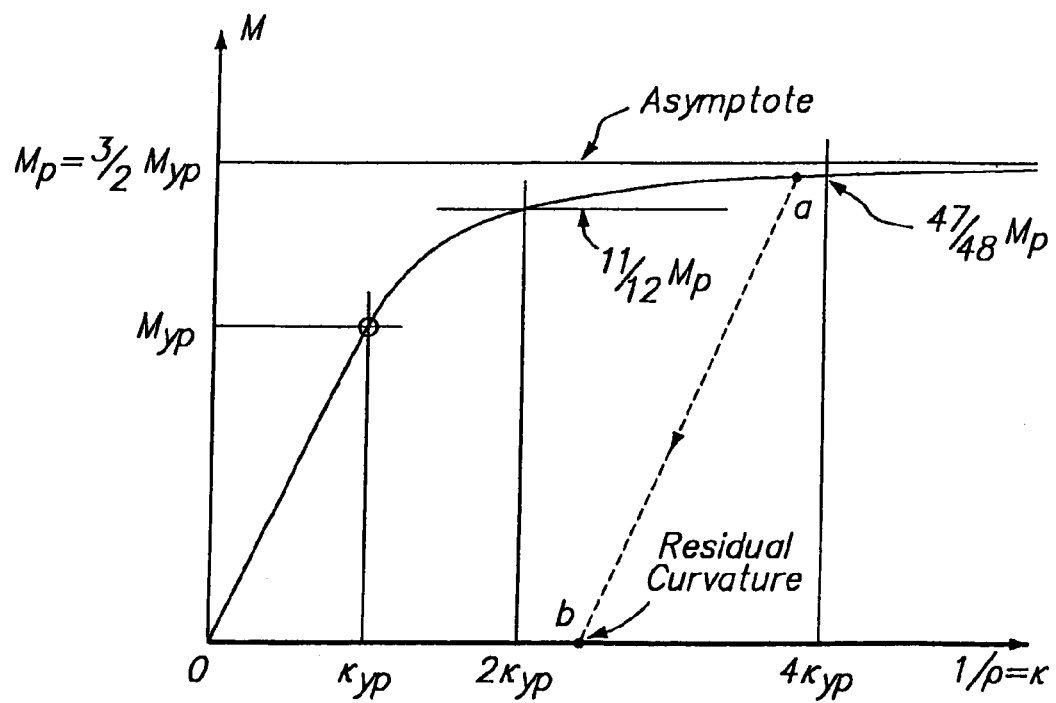
FIG. 12 is a moment verses curvature graph for a rectangular beam.

This function is plotted in FIG. 12. It may be seen in this plot that the applied moment M asymptotically approaches a limiting value $M_p$, called the plastic or ultimate moment. Beyond $^{11}/_{12} M_p$ large plastic deformations occur with little additional increase in applied moment. When the applied moment is removed, the beam rebounds elastically along a line such as a-b. Thus, the elastic portion of the total curvature approaches a limit of 3/2 the curvature at the yield point. These relations may be expressed as follows:

$$M_p = \frac{3}{2}M_{yp} \Rightarrow \kappa_{rebound} = \frac{3}{2}\kappa_{yp}$$

Imparting additional curvature in the plastic zone cannot further increase the elastic curvature, but will decrease the ratio of elastic to plastic curvature. Thus, additional curvature or larger expansion of the tissue supporting device will reduce the percentage recoil of the overall stent structure.

Figure 13:
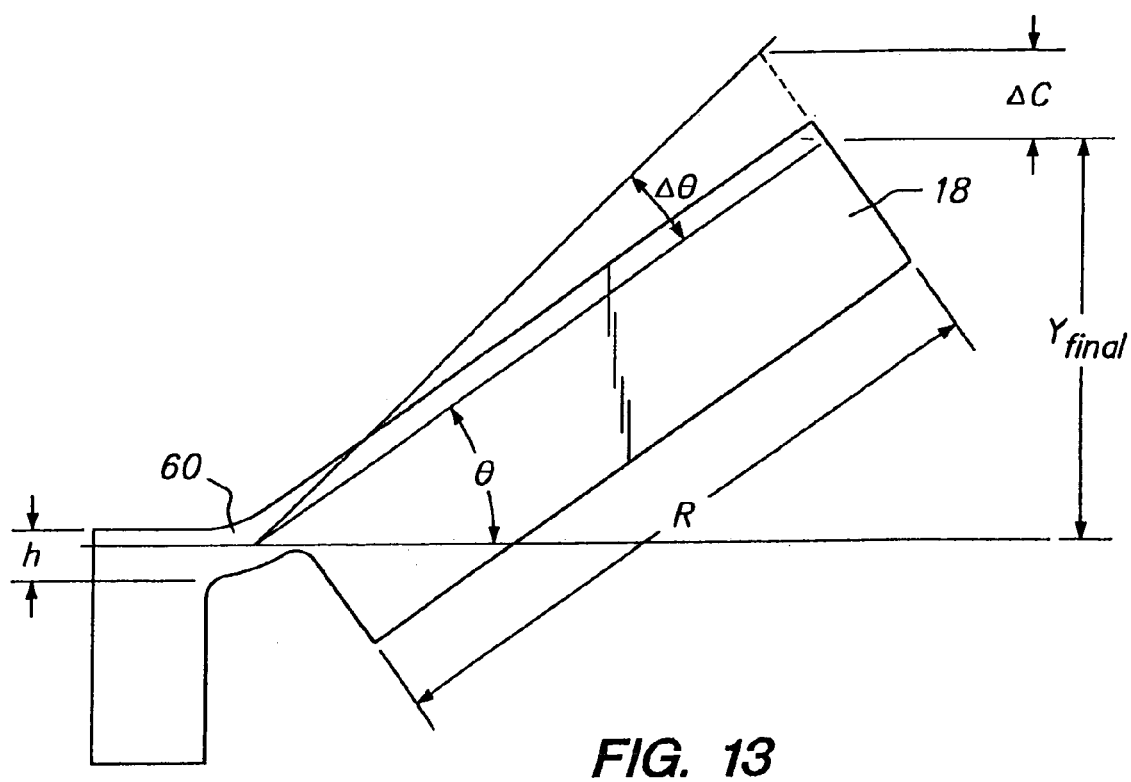
FIG. 13 is an enlarged side view of a bent ductile hinge.

As shown in FIG. 13, when a rigid strut 18 is linked to the ductile hinge 60 described above, the strut 18 forms an angle θ with the horizontal that is a function of hinge curvature. A change in hinge curvature results in a corresponding change in this angle θ. The angular elastic rebound of the hinge is the change in angle Δθ that results from the rebound in elastic curvature described above, and thus angular rebound also approaches a limiting value as plastic deformation proceeds. The following expression gives the limiting value of angular elastic rebound for the idealized hinge of FIG. 13.

$$\theta_{rebound} = 3\varepsilon_{yp}\frac{L}{h}$$

Where strain at the yield point is an independent material property (yield stress divided by elastic modulus); L is the length of the ductile hinge; and h is the width of the hinge. For non-idealized ductile hinges made of real materials, the constant 3 in the above expression is replaced by a slowly rising function of total strain, but the effect of geometry would remain the same. Specifically, the elastic rebound angle of a ductile hinge decreases as the hinge width h increases, and increases as the hinge length L increases. To minimize recoil, therefore, hinge width h should be increased and length L should be decreased.

Ductile hinge width h will generally be determined by expansion force criteria, so it is important to reduce hinge length to a practical minimum in order to minimize elastic rebound. Empirical data on recoil for ductile hinges of different lengths show significantly lower recoil for shorter hinge lengths, in good agreement with the above analysis.

The ductile hinges 20 of the tissue supporting device 10, 100, 200 provide a second important advantage in minimizing device recoil. The embodiment of FIG. 1 shows a network of struts joined together through ductile hinges to form a cylinder. As the device is expanded, curvature is imparted to the hinges 20, and the struts 18 assume an angle θ with respect to their original orientation, as shown in FIG. 13. The total circumferential expansion of the tissue supporting device structure is a function of hinge curvature (strut angle) and strut length. Moreover, the incremental contribution to stent expansion (or recoil) for an individual strut depends on the instantaneous strut angle. Specifically, for an incremental change in strut angle Δθ, the incremental change in circumference ΔC will depend on the strut length R and the cosine of the strut angle θ.

ΔC=RΔθ cos θ

Since elastic rebound of hinge curvature is nearly constant at any gross curvature, the net contribution to circumferential recoil ΔC is lower at higher strut angles θ. The final device circumference is usually specified as some fixed value, so decreasing overall strut length can increase the final strut angle θ. Total stent recoil can thus be minimized with ductile hinges by using shorter struts and higher hinge curvatures when expanded.

Empirical measurements have shown that tissue supporting device designs based on ductile hinges, such as the embodiment of FIG. 1, display superior resistance to compressive forces once expanded despite their very low expansion force. This asymmetry between compressive and expansion forces may be due to a combination of factors including the geometry of the ductile hinge, the increased wall thickness, and increased work hardening due to higher strain levels.

According to one example of the tissue supporting device of the invention, the device can be expanded by application of an internal pressure of about 2 atmospheres or less, and once expanded to a diameter between 2 and 3 times the initial diameter can withstand a compressive force of about 16 to 20 gm/mm or greater. Examples of typical compression force values for prior art devices are 3.8 to 4.0 gm/mm.

While both recoil and crush strength properties of tissue supporting devices can be improved by use of ductile hinges with large curvatures in the expanded configuration, care must be taken not to exceed an acceptable maximum strain level for the material being used. Generally, $\epsilon_{max}$ is defined as maximum strain, and it is dependent on ductile hinge width h, ductile hinge length L, and bend angle θ in radians. When strain, hinge width and bend angle are determined through other criteria, an expression may be developed to determine the required lengths for the complicated ductile hinge geometry of the present invention. Typical values for the prismatic portions of the curved ductile hinges 20 range from about 0.002 to about 0.0035 inches (0.051–0.089 mm) in hinge width and about 0.002 to about 0.006 inches (0.051–0.152 mm) in hinge length.

In many designs of the prior art, circumferential expansion was accompanied by a significant contraction of the axial length of the stent which may be up to 15% of the initial device length. Excessive axial contraction can cause a number of problems in device deployment and performance including difficulty in proper placement and tissue damage. Designs based on ductile hinges 20 can minimize the axial contraction, or foreshortening, of a tissue supporting device during expansion, as discussed in greater detail in the afore-mentioned U.S. application Ser. No. 09/183,555. This ability to control axial contraction based on hinge and strut design provides great design flexibility when using ductile hinges. For example, a stent could be designed with zero axial contraction.

The stent 10, 100, 200 of the present invention illustrates the trade off between crush strength and axial contraction. Referring to FIG. 3, a portion of the tissue supporting device 100 having an array of struts 18 and ductile hinges 20 are shown in the unexpanded state. The struts 18 are positioned initially at an angle $\theta_1$ with respect to a longitudinal axis X of the device. As the device is expanded radially from the unexpanded state illustrated in FIG. 3, the angle $\theta_1$ increases. In this case the device contracts axially from the onset of vertical expansion throughout the expansion. A higher final strut angle $\theta_1$, can significantly increase crush strength and decrease circumferential recoil of the stent structure. However, there is a trade off between increased crush strength and increase in axial contraction.

According to one example of the present invention, the struts 18 are positioned initially at an angle of about 0° to 45° with respect to a longitudinal axis of the device. As the device is expanded radially from the unexpanded state illustrated in FIG. 3, the strut angle increases to about 20° to 80°.

In addition, while ductile hinges 20 are the preferred configuration for the expandable medical device of the present invention, a stent without the defined ductile hinges would also be included within the scope of the present invention.

Figure 14:
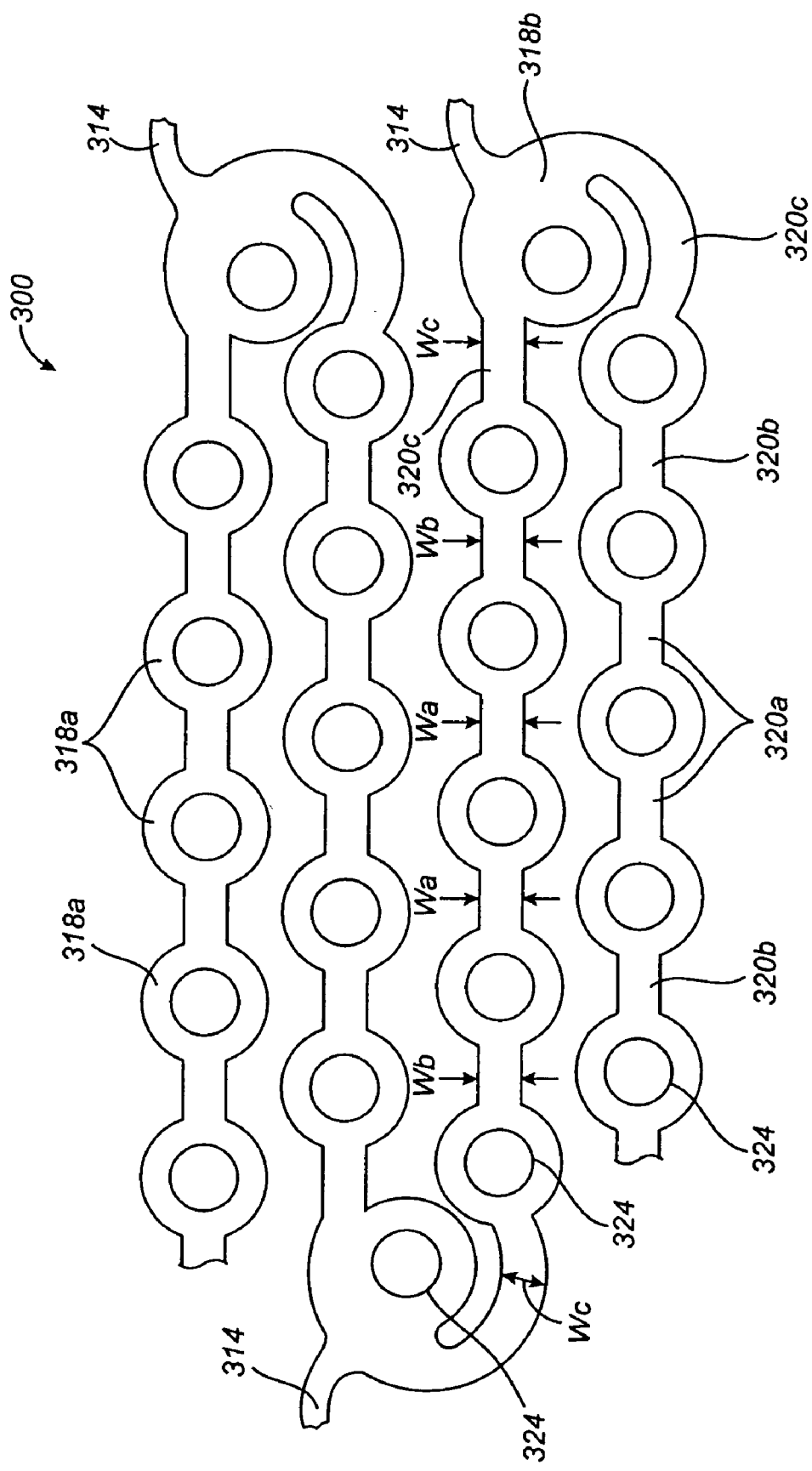
FIG. 14 is an enlarged side view of a portion of a tissue supporting device having non-deforming reservoirs and ductile hinges.

FIG. 14 illustrates an alternative embodiment of an expandable medical device or stent 300 in which the number of ductile hinges is increased and the length of the substantially non-deforming struts is decreased to form a stent with the bending forces distributed over a larger area. Such designs can be useful in stents constructed of materials which have limited ductility (elongation to failure). For example, materials having elongation to failures of less than about 35%, especially less than 25% can be used to manufacture a stent having ductile hinges when the number of ductile hinges or the total volume of material over which elastic and plastic strain energies are distributed is increased.

FIG. 14, shows a portion of an expandable cylindrical tube which is formed by a repeating pattern of interconnected hole containing sections and ductile hinges. A plurality of the cylindrical tubes of FIG. 14 can be interconnected by bridging elements 314, such as the S-shaped bridging elements shown in the embodiment of FIGS. 1 and 2. The bridging elements 314 allow the tissue supporting device to bend axially.

The stent 300 includes substantially rigid or non-deforming sections 318a and 318b interconnected by ductile hinges 320a, 320b, and 320c. The substantially non-deforming sections 318a and 318b have a width greater than widths of the adjacent ductile hinges 320a, 320b, and 320c which are reduced sections acting as stress/strain concentration features. The increased number of ductile hinges in each U-shaped section of the stent 300, compared to the previous embodiments, allows the distribution of the bending over a larger area. Less concentrated bending and less strain per area of the hinges allows the stent 300 to be designed for use with materials which have stress-strain curves lower than those of stainless steel and cobalt chromium alloys.

In the embodiment of FIGS. 1 and 2, each alternating U-shaped segment of the cylindrical tube 12 has two ductile hinges 20 which interconnect two rigid struts 18 and one rigid link 22. In contrast, the stent 300 of FIG. 14 includes in each alternating U-shaped segment at least three rigid sections 318a and 318b and at least three ductile hinges 320a–c.

The structures of the ductile hinges 320 and in particular, the widths of the hinges, are selected to distribute deformation throughout all the hinges and prevent concentrated bending in particular hinges. To achieve uniform deformation of the hinges, the hinge widths vary with the ductile hinges 320a farthest from an apex of the U-shaped segment having the smallest width Wa. The hinges 320b have a width Wb which is larger than Wa, and the hinges 320c have a width Wc which is larger than Wb. This change in the widths of the hinges is a function of the axial position of the hinge on the cylindrical element. Although uniform hinges have been shown, some or all of the hinges 320, 420 can also be tapered to further achieve uniform distribution of bending through the hinges of the structure.

As shown in FIG. 14, each of the substantially non-deforming sections 318a are circular in shape with circular openings 324 therein containing the beneficial agent. The substantially non-deforming sections 318a are staggered in adjacent legs of the U-shaped structures to achieve a compact structure. However, other shapes of the non-deforming sections 318a and the holes, such as rectangular, oval, or polygonal can also be used. The non-deforming sections 318b positioned near the apex of the U-shaped structures are formed as a part of the U-shapes. These non-deforming sections 318b can also take on different shapes. As shown the non-deforming sections 318b project to an interior of the U-shapes, however, one or more non-deforming sections can also project to an exterior of the U-shapes.

The number of openings 324 per non-deforming section 318a and 318b can be one, as shown, or two or more. In addition, non-deforming sections with different numbers and shapes of openings can be combined in one structure. In addition to the non-deforming sections containing agent within the cylindrical tubes, the bridging elements 314 can also contain one or more substantially non-deforming sections with openings therein to provide agent distributed substantially uniformly along the length of the stent.

Figure 15:
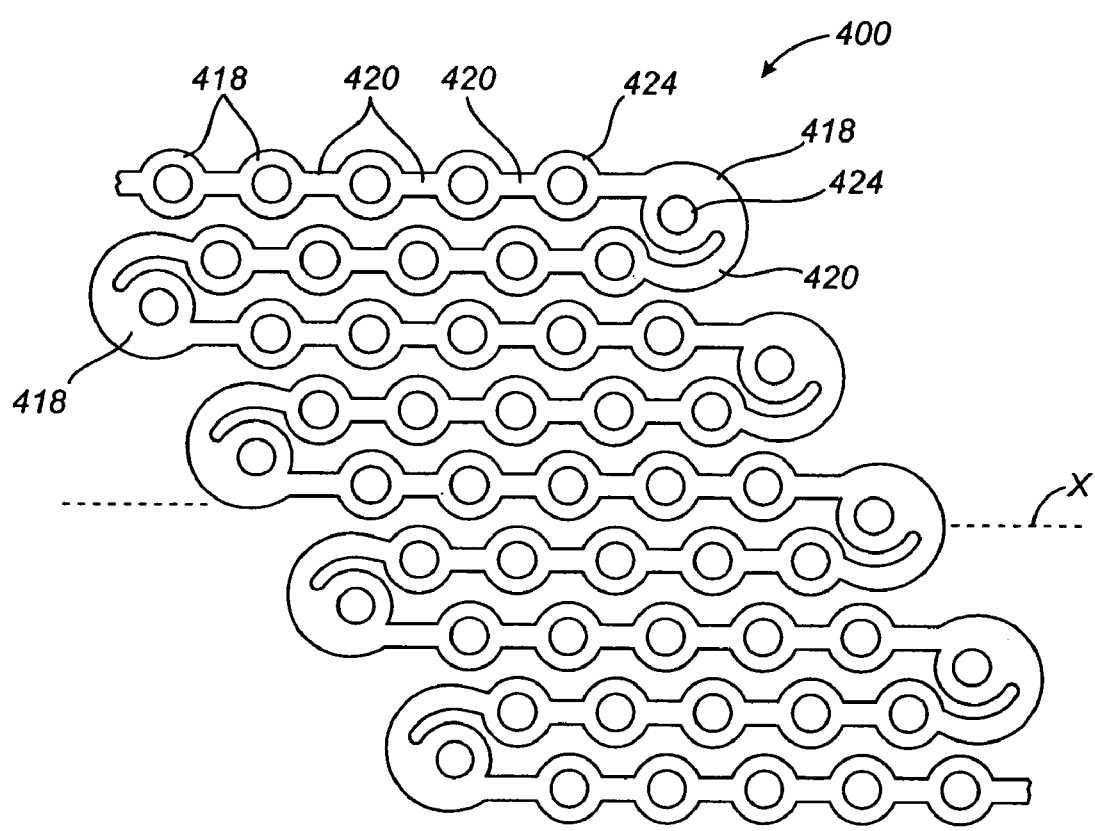
FIG. 15 is an enlarged side view of a portion of a helically wound tissue supporting device with reservoirs and ductile hinges.
Figure 16:
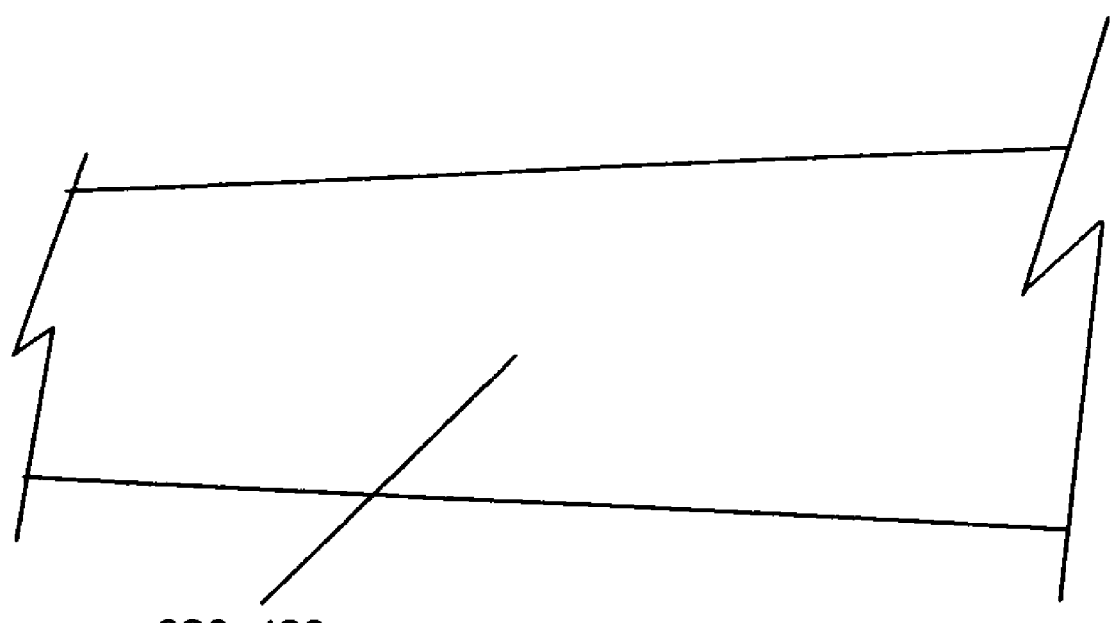
FIG. 16 illustrates an enlarged view of a portion of a ductile hinge according to yet another embodiment of the present invention.

FIG. 15 illustrates and alternative embodiment of a stent 400 having a structure formed of a plurality of interconnected U-shaped structures formed from non-deforming sections 418 and ductile hinges 420 similar to those shown in FIG. 14. The non-deforming sections 418 include one or more beneficial agent containing opening 424.

In FIG. 15, the stent 400 is shown laid flat for ease of illustration. However, when the stent is formed, such as by laser cutting from a tube, the structure illustrated in FIG. 14 is curved about a longitudinal axis X. The adjacent U-shaped structures of the stent 400 are each offset in the longitudinal direction from the adjacent U-shaped structures to form a continuous spiral ribbon or helical band. The structure of the stent 400 can eliminate or reduce the use of bridging elements by forming a continuous band of alternating U-shaped structures where the band can be formed in a cylindrical helical structure.

Therapeutic Agents

The present invention can be used for delivery of anti-restenotic agents including taxol, rapamycin, other limus drugs, cladribine, colchicines, vinca alkaloids, heparin, hinrudin and their derivatives, as well as other cytotoxic or cytostatic agents and microtubule stabilizing and microtubule inhibiting agents. Although anti-restenotic agents have been primarily described herein, the present invention may also be used to deliver other agents alone or in combination with anti-restenotic agents.

Other therapeutic agents for use with the present invention may, for example, take the form of small molecules, peptides, lipoproteins, polypeptides, polynucleotides encoding polypeptides, lipids, protein-drugs, protein conjugate drugs, enzymes, oligonucleotides and their derivatives, ribozymes, other genetic material, cells, antisense oligonucleotides, monoclonal antibodies, platelets, prions, viruses, bacteria, eukaryotic cells such as endothelial cells, stem cells, ACE inhibitors, monocyte/macrophages and vascular smooth muscle cells. Such agents can be used alone or in various combinations with one another. For instance, anti-inflammatories may be used in combination with anti-proliferatives to mitigate the reaction of tissue to the anti-proliferative. The therapeutic agent may also be a pro-drug, which metabolizes into the desired drug when administered to a host. In addition, therapeutic agents may be pre-formulated as microcapsules, microspheres, microbubbles, liposomes, niosomes, emulsions, dispersions or the like before they are incorporated into the matrix. Therapeutic agents may also be radioactive isotopes or agents activated by some other form of energy such as light or ultrasonic energy, or by other circulating molecules that can be systemically administered.

Exemplary classes of therapeutic agents include antiproliferatives, antithrombins (i.e., thrombolytics), immunosuppressants, antilipid agents, anti-inflammatory agents, antineoplastics including antimetabolites, antiplatelets, angiogenic agents, anti-angiogenic agents, vitamins, antimitotics, metalloproteinase inhibitors, NO donors, nitric oxide release stimulators, anti-sclerosing agents, vasoactive agents, endothelial growth factors, beta blockers, hormones, statins, insulin growth factors, antioxidants, membrane stabilizing agents, calcium antagonists (i.e., calcium channel antagonists), retinoids, anti-macrophage substances, antilymphocytes, cyclooxygenase inhibitors, immunomodulatory agents, angiotensin converting enzyme (ACE) inhibitors, anti-leukocytes, high-density lipoproteins (HDL) and derivatives, cell sensitizers to insulin, prostaglandins and derivatives, anti-TNF compounds, hypertension drugs, protein kinases, antisense oligonucleotides, cardio protectants, petidose inhibitors (increase blycolitic metabolism), endothelin receptor agonists, interleukin-6 antagonists, anti-restenotics, and other miscellaneous compounds.

Antiproliferatives include, without limitation, sirolimus, paclitaxel, actinomycin D, rapamycin, and cyclosporin.

Antithrombins include, without limitation, heparin, plasminogen, $\alpha_2$-antiplasmin, streptokinase, bivalirudin, and tissue plasminogen activator (t-PA).

Immunosuppressants include, without limitation, cyclosporine, rapamycin and tacrolimus (FK-506), sirolumus, everolimus, etoposide, and mitoxantrone.

Antilipid agents include, without limitation, HMG CoA reductase inhibitors, nicotinic acid, probucol, and fibric acid derivatives (e.g., clofibrate, gemfibrozil, gemfibrozil, fenofibrate, ciprofibrate, and bezafibrate).

Anti-inflammatory agents include, without limitation, salicylic acid derivatives (e.g., aspirin, insulin, sodium salicylate, choline magnesium trisalicylate, salsalate, dflunisal, salicylsalicylic acid, sulfasalazine, and olsalazine), para-amino phenol derivatives (e.g., acetaminophen), indole and indene acetic acids (e.g., indomethacin, sulindac, and etodolac), heteroaryl acetic acids (e.g., tolmetin, diclofenac, and ketorolac), arylpropionic acids (e.g., ibuprofen, naproxen, flurbiprofen, ketoprofen, fenoprofen, and oxaprozin), anthranilic acids (e.g., mefenamic acid and meclofenamic acid), enolic acids (e.g., piroxicam, tenoxicam, phenylbutazone and oxyphenthatrazone), alkanones (e.g., nabumetone), glucocorticoids (e.g., dexamethaxone, prednisolone, and triamcinolone), pirfenidone, and tranilast.

Antineoplastics include, without limitation, nitrogen mustards (e.g., mechlorethamine, cyclophosphamide, ifosfamide, melphalan, and chlorambucil), methylnitrosoureas (e.g., streptozocin), 2-chloroethylnitrosoureas (e.g., carmustine, lomustine, semustine, and chlorozotocin), alkanesulfonic acids (e.g., busulfan), ethylenimines and methylmelamines (e.g., triethylenemelamine, thiotepa and altretamine), triazines (e.g., dacarbazine), folic acid analogs (e.g., methotrexate), pyrimidine analogs (5-fluorouracil, 5-fluorodeoxyuridine, 5-fluorodeoxyuridine monophosphate, cytosine arabinoside, 5-azacytidine, and 2′,2′-difluorodeoxycytidine), purine analogs (e.g., mercaptopurine, thioguanine, azathioprine, adenosine, pentostatin, cladribine, and erythrohydroxynonyladenine), antimitotic drugs (e.g., vinblastine, vincristine, vindesine, vinorelbine, paclitaxel, docetaxel, epipodophyllotoxins, dactinomycin, daunorubicin, doxorubicin, idarubicin, epirubicin, mitoxantrone, bleomycins, plicamycin and mitomycin), phenoxodiol, etoposide, and platinum coordination complexes (e.g., cisplatin and carboplatin).

Antiplatelets include, without limitation, insulin, dipyridamole, tirofiban, eptifibatide, abciximab, and ticlopidine.

Angiogenic agents include, without limitation, phospholipids, ceramides, cerebrosides, neutral lipids, triglycerides, diglycerides, monoglycerides lecithin, sphingosides, angiotensin fragments, nicotine, pyruvate thiolesters, glycerol-pyruvate esters, dihydoxyacetone-pyruvate esters and monobutyrin.

Anti-angiogenic agents include, without limitation, endostatin, angiostatin, fumagillin and ovalicin.

Vitamins include, without limitation, water-soluble vitamins (e.g., thiamin, nicotinic acid, pyridoxine, and ascorbic acid) and fat-soluble vitamins (e.g., retinal, retinoic acid, retinaldehyde, phytonadione, menaqinone, menadione, and alpha tocopherol).

Antimitotics include, without limitation, vinblastine, vincristine, vindesine, vinorelbine, paclitaxel, docetaxel, epipodophyllotoxins, dactinomycin, daunorubicin, doxorubicin, idarubicin, epirubicin, mitoxantrone, bleomycins, plicamycin and mitomycin.

Metalloproteinase inhibitors include, without limitation, TIMP-1, TIMP-2, TIMP-3, and SmaPI.

NO donors include, without limitation, L-arginine, amyl nitrite, glyceryl trinitrate, sodium nitroprusside, molsidomine, diazeniumdiolates, S-nitrosothiols, and mesoionic oxatriazole derivatives.

NO release stimulators include, without limitation, adenosine.

Anti-sclerosing agents include, without limitation, collagenases and halofuginone.

Vasoactive agents include, without limitation, nitric oxide, adenosine, nitroglycerine, sodium nitroprusside, hydralazine, phentolamine, methoxamine, metaraminol, ephedrine, trapadil, dipyridamole, vasoactive intestinal polypeptides (VIP), arginine, and vasopressin.

Endothelial growth factors include, without limitation, VEGF (Vascular Endothelial Growth Factor) including VEGF-121 and VEG-165, FGF (Fibroblast Growth Factor) including FGF-1 and FGF-2, HGF (Hepatocyte Growth Factor), and Ang1 (Angiopoietin 1).

Beta blockers include, without limitation, propranolol, nadolol, timolol, pindolol, labetalol, metoprolol, atenolol, esmolol, and acebutolol.

Hormones include, without limitation, progestin, insulin, the estrogens and estradiols (e.g., estradiol, estradiol valerate, estradiol cypionate, ethinyl estradiol, mestranol, quinestrol, estrond, estrone sulfate, and equilin).

Statins include, without limitation, mevastatin, lovastatin, simvastatin, pravastatin, atorvastatin, and fluvastatin.

Insulin growth factors include, without limitation, IGF-1 and IGF-2.

Antioxidants include, without limitation, vitamin A, carotenoids and vitamin E.

Membrane stabilizing agents include, without limitation, certain beta blockers such as propranolol, acebutolol, labetalol, oxprenolol, pindolol and alprenolol.

Calcium antagonists include, without limitation, amlodipine, bepridil, diltiazem, felodipine, isradipine, nicardipine, nifedipine, nimodipine and verapamil.

Retinoids include, without limitation, all-trans-retinol, all-trans-14-hydroxyretroretinol, all-trans-retinaldehyde, all-trans-retinoic acid, all-trans-3,4-didehydroretinoic acid, 9-cis-retinoic acid, 11-cis-retinal, 13-cis-retinal, and 13-cis-retinoic acid.

Anti-macrophage substances include, without limitation, NO donors.

Anti-leukocytes include, without limitation, 2-CdA, IL-1 inhibitors, anti-CD116/CD18 monoclonal antibodies, monoclonal antibodies to VCAM, monoclonal antibodies to ICAM, and zinc protoporphyrin.

Cyclooxygenase inhibitors include, without limitation, Cox-1 inhibitors and Cox-2 inhibitors (e.g., CELEBREX® and VIOXX®).

Immunomodulatory agents include, without limitation, immunosuppressants (see above) and immunostimulants (e.g., levamisole, isoprinosine, Interferon alpha, and Interleukin-2).

ACE inhibitors include, without limitation, benazepril, captopril, enalapril, fosinopril sodium, lisinopril, quinapril, ramipril, and spirapril.

Cell sensitizers to insulin include, without limitation, glitazones, P par agonists and metformin.

Antisense oligonucleotides include, without limitation, resten-NG.

Cardio protectants include, without limitation, VIP, pituitary adenylate cyclase-activating peptide (PACAP), apoA-I milano, amlodipine, nicorandil, cilostaxone, and thienopyridine.

Petidose inhibitors include, without limitation, omnipatrilat.

Anti-restenotics include, without limitation, include vincristine, vinblastine, actinomycin, epothilone, paclitaxel, and paclitaxel derivatives (e.g., docetaxel).

Miscellaneous compounds include, without limitation, Adiponectin.

While the invention has been described in detail with reference to the preferred embodiments thereof, it will be apparent to one skilled in the art that various changes and modifications can be made and equivalents employed, without departing from the present invention.

What is claimed is:

1. An expandable medical device comprising:
   at least one cylindrical tube;
   a plurality of substantially rigid sections interconnected to form the at least one cylindrical tube;
   a plurality of ductile hinges formed between the substantially rigid sections, the ductile hinges allowing the cylindrical tube to be expanded or compressed from a first diameter to a second diameter by deformation of the ductile hinges without substantial deformation of the substantially rigid sections; and
   a plurality of openings in the plurality of substantially rigid sections, the plurality of openings containing at least one beneficial agent, none of said openings located on said plurality of ductile hinges, wherein the ductile hinges are designed to deform plastically upon radial expansion or compression of the expandable medical device while the plurality of substantially rigid sections experience substantially no plastic deformation upon radial expansion or compression.

2. The expandable medical device according to claim 1, wherein said plurality of beneficial agent containing openings are non-deforming openings.

3. The expandable medical device according to claim 1, wherein the plurality of beneficial agent containing openings extend through a thickness of the at least one cylindrical tube, so as to thereby define a through-opening.

4. The expandable medical device according to claim 1, wherein the plurality of beneficial agent containing openings have a depth less than a thickness of the at least one cylindrical tube, so as to thereby define a recess.

5. The expandable medical device according to claim 1, wherein a single beneficial agent containing opening is located in each of the plurality of rigid sections.

6. The expandable medical device according to claim 1, wherein a plurality of beneficial agent containing openings are located in each of the plurality of rigid sections.

7. The expandable medical device according to claim 1, wherein the plurality of substantially rigid sections and the plurality of ductile hinges are interconnected in a plurality of alternating interconnected U-shapes to form the at least one cylindrical tube.

8. The expandable medical device according to claim 7, wherein the interconnected U-shapes each include at least three substantially rigid sections and at least two ductile hinges.

9. The expandable medical device according to claim 7, wherein the interconnected U-shapes each include at least four substantially rigid sections and at least three ductile hinges.

10. The expandable medical device according to claim 7, wherein ductile hinges closer to bases of the interconnected U-shapes have a larger width than ductile hinges farther from the bases of the interconnected U-shapes.

11. The expandable medical device according to claim 7, wherein the interconnected U-shapes are asymmetrical.

12. The expandable medical device according to claim 1, wherein the ductile hinges have different widths depending on their location in the stent.

13. The expandable medical device according to claim 1, wherein a width of the ductile hinges varies depending on a position of the ductile hinge on the at least one cylindrical tube in an axial direction.

14. The expandable medical device according to claim 13, wherein a width of the ductile hinges closest to the ends of the at least one cylindrical tube is greater than a width of the ductile hinges closest to the center of the at least one cylindrical tube.

15. The expandable medical device according to claim 1, wherein the plurality of ductile hinges are sized such that a width of each of the plurality of ductile hinges closest to the ends of the at least one cylindrical tube is greater than a width of the ductile hinges closest to the center of the at least one cylindrical tube.

16. The expandable medical device according to claim 1, wherein said beneficial agent includes antiproliferatives.

17. The expandable medical device according to claim 1, wherein said at least one cylindrical tube includes two cylindrical tubes interconnected by a bridging element.

18. The expandable medical device according to claim 17, wherein the bridging element includes at least one flexible segment and at least one substantially rigid section having a beneficial agent containing opening.

19. The expandable medical device according to claim 1, wherein the plurality of ductile hinges are tapered such that a width of each of the plurality of ductile hinges closest to the ends of the at least one cylindrical tube is greater than a width of the ductile hinges closest to the center of the at least one cylindrical tube.

20. An expandable stent comprising:
   a plurality of substantially rigid sections;
   a plurality of ductile hinges interconnecting the plurality of substantially rigid sections to form a cylindrical stent which is expandable from a first diameter to a second diameter by deformation of the plurality of ductile hinges without substantial deformation of the substantially rigid sections; and a plurality of openings containing at least one beneficial agent, the openings positioned in the substantially rigid sections, none of said openings located on said plurality of ductile hinges, wherein the ductile hinges are designed to deform plastically upon radial expansion or compression of the expandable medical device while the plurality of substantially rigid sections experience substantially no plastic deformation upon radial expansion or compression.

21. The expandable stent according to claim 20, wherein said plurality of openings are non-deforming openings.

22. The expandable stent according to claim 20, wherein the plurality of openings extend through a thickness of the at least one cylindrical tube, so as to thereby define a through-opening.

23. The expandable stent according to claim 20, wherein the plurality of openings have a depth less than a thickness of the at least one cylindrical tube, so as to thereby define a recess.

24. The expandable stent according to claim 20, wherein a single beneficial agent containing opening is located in each of the plurality of rigid sections.

25. The expandable stent according to claim 20, wherein a plurality of beneficial agent containing openings are located in each of the plurality of rigid sections.

26. The expandable stent according to claim 20, wherein the plurality of substantially rigid sections and the plurality of ductile hinges are interconnected in a plurality of alternating interconnected U-shapes.

27. The expandable stent according to claim 26, wherein the plurality of alternating interconnected U-shapes form a cylindrical tube.

28. The expandable stent according to claim 26, wherein the plurality of alternating interconnected U-shapes form a helically wound band.

29. The expandable stent according to claim 26, wherein the interconnected U-shapes each include at least four substantially rigid sections and at least three ductile hinges.

30. The expandable stent according to claim 26, wherein the ductile hinges have different widths depending on their location in the interconnected U-shapes.

31. The expandable stent according to claim 30, wherein ductile hinges closer to bases of the interconnected U-shapes have a larger width than ductile hinges farther from the bases of the interconnected U-shapes.

32. The expandable stent according to claim 20, wherein a width of the ductile hinges varies depending on a position of the ductile hinge on the cylindrical stent in an axial direction.

33. The expandable stent according to claim 32, wherein a width of the ductile hinges closest to the ends of the cylindrical stent is greater than a width of the ductile hinges closest to the center of the cylindrical stent.

34. The expandable stent according to claim 20, wherein the plurality of ductile hinges are tapered such that a width of each of the plurality of ductile hinges closest to the ends of the at least one cylindrical tube is greater than a width of the ductile hinges closest to the center of the at least one cylindrical tube.

* * * * *